United States Patent
Reuling et al.

(10) Patent No.: US 10,306,850 B2
(45) Date of Patent: Jun. 4, 2019

(54) YIELD QTLS IN CUCUMBER PLANTS

(71) Applicant: NUNHEMS B.V., Nunhem (NL)

(72) Inventors: Gerhard T. M. Reuling, Heythuysen (NL); Peter Arnold Gijsbert Kraan, Buggenum (NL); Frank Beenders, Roggel (NL); Marion Van De Wal, Best (NL); Freddy Hermans, Sevenum (NL); Hans-Peter Koelewijn, Veenendaal (NL); Steven D. Tanksley, Ithaca, NY (US); Alexandra M. Casa, Ithaca, NY (US)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/519,446

(22) PCT Filed: Oct. 14, 2015

(86) PCT No.: PCT/EP2015/073742
§ 371 (c)(1),
(2) Date: Apr. 14, 2017

(87) PCT Pub. No.: WO2016/059092
PCT Pub. Date: Apr. 21, 2016

(65) Prior Publication Data
US 2017/0238492 A1 Aug. 24, 2017

(30) Foreign Application Priority Data
Oct. 16, 2014 (EP) ..................................... 14189200

(51) Int. Cl.
*A01H 5/08* (2018.01)
*A01H 1/04* (2006.01)
*C12Q 1/6895* (2018.01)
*A01H 1/02* (2006.01)

(52) U.S. Cl.
CPC ................. *A01H 5/08* (2013.01); *A01H 1/02* (2013.01); *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2010/0313291 A1    12/2010 De Haan et al.

FOREIGN PATENT DOCUMENTS

WO    WO 2009/082222 A1    7/2009

OTHER PUBLICATIONS

Fazio et al 2003 Theor Appl Genet 107:864-874 provided by Applicant (Year: 2003).*
Yuan et al 2008 Euphytica 164:473-491 provided by Applicant (Year: 2008).*
Allen et al., Transcript-specific, single-nucleotide polymorphism discovery and linkage analysis in hexaploid bread wheat (*Triticum aestivum* L.), Plant Biotechnology, 2011, J. 9, pp. 1086-1099.
Cucumber_v2 database, http://www.icugi.org/cgi-bin/gb2/gbrowse/cucumber_v2/, last accessed on Mar. 28, 2017 (1 page).
European Search Report issued in European Patent Application No. 14189200 dated Apr. 8, 2015 (6 pages).
Fazio et al., "Genetic mapping and QTL analysis of horticultural traits in cucumber (*Cucumis sativus* L.) using recombiant inbred lines", Theor Appl Genet, 2003, vol. 107, pp. 864-874.
Henikoff et al., "Amino acid substitution matrices from protein blocks", PNAS, 1992, vol. 89, pp. 10915-10919.
Huang et al., "The genome of the cucumber, *Cucumis sativus* L.", Nature Genetics, 2009, vol. 41, No. 12, pp. 1275-1283.
International Search Report and Written Opinion issued in International Patent Application No. PCT/EP2015/073742 dated Jan. 15, 2016 (12 pages).
Ji et al., "Ty-3, a begomovirus resistance locus near the Tomato yellow leaf curl virus resistance locus Ty-1 on chromosome 6 of tomato", Mol. Breeding, 2007, vol. 20, pp. 271-284.
Qi et al., "A genome variation map provides insights into the genetic basis of cucumber domestication and diversity", Nature Genetics, Dec. 2013, vol. 45, No. 12, pp. 1510-1518.
Shetty et al., "Screening the Cucumber Germplasm Collection for Fruit Yield and Quality", CropSci., 2002, vol. 42, pp. 2174-2183.
The United States Standards for Grades of Cucumbers, US Department of Agriculture, Effective Sep. 6, 2016, pp. 1-8.
Verlaan et al., "Chromosomal rearrangements between tomato and Solanum chilense hamper mapping and breeding of the TYLCV resistance gene Ty-1", The Plant Journal, 2011, vol. 68, pp. 1093-1103.
Yuan et al., "Genetic mapping and QTL analysis of fruit and flower related traits in cucumber (*Cucumis sativus* L.) using recombinant inbred lines", Euphytica 2008, vol. 164, pp. 473-491.

* cited by examiner

Primary Examiner — Brent T Page
(74) Attorney, Agent, or Firm — Arent Fox LLP

(57) ABSTRACT

The present invention relates to cultivated cucumber plants comprising a yield QTL on chromosome 2 and/or chromosome 6 of their genome.

27 Claims, No Drawings
Specification includes a Sequence Listing.

SEQUENCE LISTING

<160> NUMBER OF SEQ ID NOS: 30

<210> SEQ ID NO 1
<211> LENGTH: 150
<212> TYPE: DNA
<213> ORGANISM: Cucumis sativus

<400> SEQUENCE: 1

```
aaatttatta aagtcttttt ttctctctcg atcatatatt atttatatat ttgttatctt    60
ttaacccttt gaacgatata gttcttaatt aaaagtatag gagttgcaac aaaagatgga   120
acagccatac catatccaaa accaatccac                                    150
```

<210> SEQ ID NO 2
<211> LENGTH: 150
<212> TYPE: DNA
<213> ORGANISM: Cucumis sativus

<400> SEQUENCE: 2

```
taaaaggttt aaatgtgatc ataaagaatt ccatctatct atatttcatt tattaatgtt    60
gtcaacagta ataagaagca tttaactcta tgtaaaaaga tgaaacaaac aaaaagtaac   120
tcataacttc aatagatttc ttaccatctm                                    150
```

<210> SEQ ID NO 3
<211> LENGTH: 150
<212> TYPE: DNA
<213> ORGANISM: Cucumis sativus

<400> SEQUENCE: 3

```
caaaaaaaaa caaaaatcaa aaaaaggaaa ttcataaaaa cctaaagccc taaaccctaa    60
ttcgctaaaa aagagaccta attttacgga aaagaaaaga actaacctag agatgacgtg   120
gcatyagatt ttctctgggt cccatttaa                                    150
```

<210> SEQ ID NO 4
<211> LENGTH: 150
<212> TYPE: DNA
<213> ORGANISM: Cucumis sativus

<400> SEQUENCE: 4 tattgtttt gtggacgtat gattatctta aaaattactt ctaatatata tttggtgaag      60
caagtttttc taaggttaaa ataaacaata cctccaaaca acttagaaaa atgactttta     120
ttgatgtaat saaaaaaata aaatgatctc                                     150

<210> SEQ ID NO 5
<211> LENGTH: 150
<212> TYPE: DNA
<213> ORGANISM: Cucumis sativus

<400> SEQUENCE: 5
tcatasaatg atgataactt tgtgagcaat gtaacacaaa gttaggttta aacttacttt      60
ttttcatcta aattctgtca tttggtcata tggatacgtt tgtttaaaaa caataataat     120
aaagtagrtt agtgttaakg ctatatagat                                     150

<210> SEQ ID NO 6
<211> LENGTH: 150
<212> TYPE: DNA
<213> ORGANISM: Cucumis sativus

<400> SEQUENCE: 6
kcaaatgttt tctcttctaa ttttttttaa cataataaaa gatagagtac aaatagaaat      60
agtaaatcga aaaataaaaa ctaaatatta cgaattttga taaaactgaa ggaacaacga     120
aatagaaaaa gcaaggatgt tgctgcaaat                                     150

<210> SEQ ID NO 7
<211> LENGTH: 150
<212> TYPE: DNA
<213> ORGANISM: Cucumis sativus

<400> SEQUENCE: 7
catgtcaatc tcaaagtcta ttcacaaaaa atacaccatt tgagggaaga gggataatta      60
caaggaaaag aaaagcagtg actaagtgaa aacaaataca agatttcatt ttccacttat     120
gacttcaatt tcaaagatct ttcgrtctat                                     150

<210> SEQ ID NO 8
<211> LENGTH: 150
<212> TYPE: DNA
<213> ORGANISM: Cucumis sativus

<400> SEQUENCE: 8
rcatcaacma aaaaaaamma aaaaggatcc atcttgttca acacgattgc cactttccc       60 tttggtccat ttggttggag agaaacaatc aaatattcag caacaaagcc tgaacataga     120
ctgaattatg ggaagacatt aaatctctca                                     150

<210> SEQ ID NO 9
<211> LENGTH: 150
<212> TYPE: DNA
<213> ORGANISM: Cucumis sativus

<400> SEQUENCE: 9

```
tggtgcttcc ttttcctcac ttttttttta aattatgaaa tctcttaaca gagtattcaa      60
ggaaaagaag tgtgctataa aataaaactc tctaagacta aagatatcta tttgataact     120
acttttttct ttttgtcata gacatagcta                                      150

<210> SEQ ID NO 10
<211> LENGTH: 150
<212> TYPE: DNA
<213> ORGANISM: Cucumis sativus

<400> SEQUENCE: 10
ctgtaaaaat atatacctag ttcctagatt ccaaccagac aagttagcag cagtagttaa      60
agcttccctc caaagttggg tctttgtttg aacttaggc tgatgtttgg ccagtgcttc      120
tccgaagcta ccagtttgtt ttcgtatatc                                      150

<210> SEQ ID NO 11
<211> LENGTH: 150
<212> TYPE: DNA
<213> ORGANISM: Cucumis sativus

<400> SEQUENCE: 11
tcgggataak tttgattttg aaaatccatt tgttagaaat tagaaagggt gcatctcaat      60
ttacacaaag cttaaacatt ctagttggga tgttcttttt gtcaaccgga aaggagaaaa    120
acatctaaca aaaatcgaay gattacattc                                      150

<210> SEQ ID NO 12
<211> LENGTH: 150
<212> TYPE: DNA
<213> ORGANISM: Cucumis sativus

<400> SEQUENCE: 12
aatgcagtat gaaccagmgg gagatgagct ttcctgataa tgatcttttg ttttgattcc      60
aatggaccaa aaaacatat ggagaatgaa aactaaacaa accaaataag aaggcatcta    120
gactagtgtt tgccatgtac tcatagacaa                                      150

<210> SEQ ID NO 13
<211> LENGTH: 150
<212> TYPE: DNA
<213> ORGANISM: Cucumis sativus

<400> SEQUENCE: 13
aacataatta tacctttta tcgctaccac ctgttaccaa caattataag cttgatgtag      60
ggttggaata atgtaatcaa attccaaaca taatagtaca taaaaacaaa actattttat    120
ttatttgttt gttattyarg tcaagatctt                                      150

<210> SEQ ID NO 14
<211> LENGTH: 150
<212> TYPE: DNA
<213> ORGANISM: Cucumis sativus

<400> SEQUENCE: 14
atcwtgcact aaagcaaatt aagactgttt ttgcaaagtt aaacaagctt gagaaacttc      60
ttgtagagtc cctgggtaaa gatttgagct gtgagttacg gaattaagcc agacagacaa    120
cccattgtca acaccatttt ggtttaatct                                      150

<210> SEQ ID NO 15
<211> LENGTH: 150
```

```
<212> TYPE: DNA
<213> ORGANISM: Cucumis sativus

<400> SEQUENCE: 15
tcttctctaa ccaatgttag aswttgtttg tgtctaacat atgtatcatg tacacagcgg      60
ctggcttgcg aaactggtct cctgaaaaca aagcagtcat tgtaagtgaa gttgagaaga    120
tagtttggcc agccattgca gcaggcragg                                      150

<210> SEQ ID NO 16
<211> LENGTH: 150
<212> TYPE: DNA
<213> ORGANISM: Cucumis sativus

<400> SEQUENCE: 16
aattaaaccc ataatttgat aaagaaataa aattaaaaga agaaagagtg tgacgtggct      60
ttcccaaatc gaataatggg attccatctg gaagcttcca cagtgttctg gatctctgtt    120
gttcttccag actcatcctt ctgaaccccct                                     150

<210> SEQ ID NO 17
<211> LENGTH: 150
<212> TYPE: DNA
<213> ORGANISM: Cucumis sativus

<400> SEQUENCE: 17
aatggaatta tggttggayt tttgttaata ggtatgaaaa caaatttttta tgtttccatt     60 aaaagggacg tccttctata atatatgcaa attaattaag ggtattaagg gtgagaaaaa   120
attatatatt aattgttgga catttgtatt                                     150

<210> SEQ ID NO 18
<211> LENGTH: 150
<212> TYPE: DNA
<213> ORGANISM: Cucumis sativus

<400> SEQUENCE: 18
ataatagaag aggagggcat gagtggaaga aacaagttca tctgctgaag aagtttttgat    60 attgagttca taatcctgaa gagattgcag attcatggtg taaaatgcta acgagattta   120
agtcttatta ggagattgta aaagaaaaac                                     150

<210> SEQ ID NO 19
<211> LENGTH: 150
<212> TYPE: DNA
<213> ORGANISM: Cucumis sativus

<400> SEQUENCE: 19
rtatgtatag gattgcagga tgaytcttta taggagtaat agtgggagga tcaacactaa     60
ttttattgtt tcacaacctc tgcttttaga aggaaagcaa ttcatagatt taaataatct   120
cccagtcgga aaattcatca ttttgaatgg                                     150

<210> SEQ ID NO 20
<211> LENGTH: 150
<212> TYPE: DNA
<213> ORGANISM: Cucumis sativus

<400> SEQUENCE: 20
aggtgaactt gtgacataga taaaagaat tattatttta gggtttagaa agacacaact      60
ttactgctac tataagtgtg agttccataa atgagagaca acattagagg acaccaaccc   120
```
aatttaaacc taaattaaaa gggttagagc                                            150

<210> SEQ ID NO 21
<211> LENGTH: 150
<212> TYPE: DNA
<213> ORGANISM: Cucumis sativus

<400> SEQUENCE: 21
ttcctcaacg atttgtagcc tttgtgacgg ttgggagtgc tgatacgggc caacttggaa           60
aagatcttga gaaggcggcg gtggcaggtg tagagagagc ggttaatggt ggcaacgaca          120
gcggaggggg cattcttgat tggagacttg                                            150

<210> SEQ ID NO 22
<211> LENGTH: 150
<212> TYPE: DNA
<213> ORGANISM: Cucumis sativus

<400> SEQUENCE: 22
tttggcaaaa ctcagagaat caagaaggat ttgggcagct ttttgtggta tcggaggagc           60
agaagcttga ttggccagac atgttctaca taaccactct ccctcttaat ctaaggaagc          120
ctcatctttt tcaaaggctt ccaccaaaac                                            150

<210> SEQ ID NO 23
<211> LENGTH: 150
<212> TYPE: DNA
<213> ORGANISM: Cucumis sativus

<400> SEQUENCE: 23
gaaaatakaa ttttcttccc aaagactcaa aatccaccca tctccagccg tcatctctca           60
cgaatttcgc acggaccctc aaaatacaa ttcttctcca acattatacc gccactctct          120
ttttttattt ctttattatt tcaatatata                                            150

<210> SEQ ID NO 24
<211> LENGTH: 150
<212> TYPE: DNA
<213> ORGANISM: Cucumis sativus

<400> SEQUENCE: 24
tgtaaaattt aatggcaaaa aacttatgaa acaaaacaag ttattataat atttaatgaa           60 gattttctt ctttcgcttt attataatat ttggagatgt tgaagacaaa atgcataaaa          120 ttctaaaatat tggatggaaa cgttggagca                                           150

<210> SEQ ID NO 25
<211> LENGTH: 150
<212> TYPE: DNA
<213> ORGANISM: Cucumis sativus

<400> SEQUENCE: 25
aatgagagct atcataatta ttgcaataat attgttcttt ttatttgggg ctcttttaat           60
tttttttatg tattggtatt taagtaaaat catttgagtt aaatcactaa caaagaattg          120
agaaattcaa taatgaccaa agggaactga                                            150

<210> SEQ ID NO 26
<211> LENGTH: 150
<212> TYPE: DNA
<213> ORGANISM: Cucumis sativus

<400> SEQUENCE: 26

```
cctctgtttc agcttccaca acttgtatga tcttgcaccc ttcaagctct tcgataccag        60
gtgtgtgttt tttccactat aacctaaacc ctcgcaatgt ttcaagaaag ggtatgtgtg       120
tttttgtgat tttattcaga ttgaactctc                                        150

<210> SEQ ID NO 27
<211> LENGTH: 150
<212> TYPE: DNA
<213> ORGANISM: Cucumis sativus

<400> SEQUENCE: 27
gggattcatc atyatgtamg aagagtatca acttgtaggg atatttcttt ataacccaga        60
tcaatttcag ttttaataga cgtgatcaca cgtgagtata gcatgctcta tttatgcata       120
atgctaagcg agtggtttta tctmygagga                                        150

<210> SEQ ID NO 28
<211> LENGTH: 150
<212> TYPE: DNA
<213> ORGANISM: Cucumis sativus

<400> SEQUENCE: 28
acacaattta tctcttcttc aycactgggg gacccggcaa cacttctctt tcttgtcgtc        60
ttcacgttct ttaactaatt tcacttctgc cctgcttcaa tagtaagtgt tttgtctgtt       120
tttctgctgt tttcattttt tcctttttg                                         150

<210> SEQ ID NO 29
<211> LENGTH: 150
<212> TYPE: DNA
<213> ORGANISM: Cucumis sativus

<400> SEQUENCE: 29
cataaattat aagcatccaa ttacataaaa taaagtccct accaactttg ttatgtggtc        60
aaaacagtca tcttctatgt atatataact cattaatata tataagttta tattcctaaa       120
ttggatttgt gtggatatta taaaagttya                                        150

<210> SEQ ID NO 30
<211> LENGTH: 150
<212> TYPE: DNA
<213> ORGANISM: Cucumis sativus

<400> SEQUENCE: 30
gatttgattt tcttggtgct tgttgatctg ttctgctaat taagcatatt tttatgaaat        60
ttataccgtc tgaatttaaa ttttaatgtg gatgagttac taatattatt ggaagcttgc       120
agatgttgtg agggatgatc ctacgaacaa                                        150
```

YIELD QTLS IN CUCUMBER PLANTS

CROSS REFERENCE TO RELATED APPLICATIONS

This application is a 35 U.S.C. 371 National Phase of PCT Application No. PCT/EP2015/073742 filed Oct. 14, 2015, which claims benefit to European patent application No. 14189200.0 Oct. 16, 2014, the disclosure of which hereby incorporated by reference in its entirety.

FIELD

The present invention relates to the field of cucumber breeding. Provided are two Quantitative Trait Loci (QTL) located on chromosome 2 and chromosome 6 of the cucumber genome, which can be used to increase yield in cultivated cucumbers (*Cucumis sativus* var. *sativus*), such as pickling cucumbers (e.g. American pickling, European pickling types), slicing cucumbers (e.g. American slicing), long cucumbers, short cucumbers, European greenhouse cucumbers, Beit-Alpha type cucumbers, oriental trellis type cucumbers (also marketed as 'burpless'), Asian cucumbers (which can be further subdivided into different types, such as Indian Mottled cucumber, Chinese Long cucumber, Korean cucumber and Japanese cucumber types, whereby the first belongs to the Indian cucumber group and the last three are part of the East Asian cucumber group). The two QTLs are referred herein as QTL2.1 and QTL6.1. Also provided are cultivated cucumber plants comprising (an) introgression fragment(s) on chromosomes 2 and/or chromosome 6 comprising QTL2.1 and/or QTL6.1, whereby the introgression fragment(s) significantly increase the fruit yield of the cultivated cucumber comprising the introgression(s) compared to the same cultivated cucumber lacking the introgression(s). Also one or more molecular markers (especially Single Nucleotide Polymorphisms or SNPs) which are present on the introgression fragment(s) and which are indicative of the presence of the introgression fragment(s) and methods of using such markers are provided herein. Likewise seeds, plant parts, cells and/or tissues comprising QTL2.1 and/or QTL6.1 in their genome and comprising otherwise a genome of cultivated cucumber in their genome are provided. In one aspect QTL2.1 and/or QTL6.1 (i.e. the introgression fragment comprising the QTL) is present in heterozygous form in a cultivated cucumber plant, cell or tissue. In another aspect QTL2.1 and/or QTL6.1 (i.e. the introgression fragment comprising the QTL) is present in homozygous form in a cultivated cucumber plant, cell or tissue. In a specific aspect the cultivated cucumber plant is an F1 hybrid, especially an F1 hybrid generated by crossing two inbred parent lines, whereby at least one of the parent lines comprises the QTL2.1 and/or QTL6.1 (i.e. the introgression fragment comprising the QTL) in homozygous form.

BACKGROUND

Cultivated cucumber (*Cucumis sativus* var. *sativus* L.) is an important vegetable crop worldwide. It belongs to the family Cucurbitaceae. It is thought to originate from South East Asia from wild ancestors with small, bitter fruits, such as *Cucumis sativus* var. *hardwickii*.

The cultivated cucumber genome has seven pairs of chromosomes (n=7) and a haploid genome size of about 367 Mb (Megabases) with an estimated total of about 26,682 genes. The cucumber genome was the first vegetable genome to be sequenced (Huang et al. 2009, Nature Genetics, Volume 41, Number 12, p 1275-1283 and http://www.icugi.org/cgi-bin/gb2/gbrowse/cucumber_v2/).

Yield of cultivated cucumber has not increased much over the last decades. Shetty and Wehner 2002 (CropSci. 42: 2174-2183) screened the USDA cucumber germplasm collection for fruit quality and fruit yield under field conditions in North Carolina (USA) and suggest that high yielding cultigens identified in their study can be used to develop high yielding cultivars.

WO2009/082222 used on of the accessions identified by Shetty and Wehner in 2002 (supra), the Turkish Beit-Alpha landrace PI 169383 to identify QTLs for fruit weight of harvest stage cucumbers on linkage group 3 and/or 4 of PI 69383.

Yuan et al. 2008 (Euphytica 164: 473-491) genetically mapped specific fruit traits in a cross between a Northern Chinese Cucumber S94 and a NorthWest European Cucumber S06. Their linkage group 3 appears to correspond to the physical chromosome 2 and their linkage group 2 appears to correspond to the physical chromosome 6. They mapped a locus called fw2.1 (fruit weight) to the top of chromosome 6 (LG2) and they mapped a locus called fw3.1 (fruit weight) to the bottom of chromosome 2 (LG3). However, they did not map total fruit yield.

Fazio et al. 2003 (Theor Appl Genet 107: 864-874) genetically mapped a number of traits, including cumulative fruits per plants over three harvests and morphological traits such as little leaf ('ll'). Their linkage group 1 appears to correspond to the physical chromosome 6. A locus called fpl1.2 (fruits per plant) was consistent in both environments and mapped to the little leaf locus. Little leaf is physically located in the region spanning 7 Mb and 8.5 Mb of the physical chromosome 6, i.e. it is at the top of chromosome 6.

Still, there remains a need for identifying QTLs for fruit yield in cucumber to be able to increase fruit yield of modern cucumber varieties.

GENERAL DEFINITIONS

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested cucumber fruits or parts thereof), flowers, leaves, seeds, tubers, bulbs, clonally propagated plants, roots, rootstocks, stems, root tips and the like. Also any developmental stage is included, such as seedlings, immature and mature, etc. When "seeds of a plant" are referred to, these either refer to seeds from which the plant can be grown or to seeds produced on the plant, after self-fertilization or cross-fertilization.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). Thus, for example reference may herein be made to a "yield allele" of the yield locus QTL2.1 or QTL6.1.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a QTL, a gene or genetic marker is found. The yield locus (or yield-increasing locus) is, thus, the location in the genome of cucumber, where QTL2.1 or QTL6.1 are found. In cultivated cucumber the QTLs are found on chromosome 2 and on chromosome 6, respectively (using the chromosome assignment of Huang et al. 2009, Nature Genetics, Volume 41, Number 12, p 1275-1283 and http://www.icugi.org/cgi-bin/gb2/gbrowse/cucumber_v2/) i.e. they are introgressed into the cultivated cucumber genome (i.e. onto chromosome 2 and 6) from wild or primitive cucumber accessions.

A "quantitative trait locus", or "QTL" is a chromosomal locus that encodes for one or more alleles that affect the expressivity of a continuously distributed (quantitative) phenotype. The yield conferring quantitative trait loci (or "yield QTLs") are named herein QTL2.1 and QTL6.1.

"Cucumber genome" and "physical position on the cucumber genome" and "chromosome 2" and/or on "chromosome 6" refers to the physical genome of cultivated cucumber, world wide web at icugi.org/cgi-bin/gb2/gbrowse/cucumber_v2/, and the physical chromosomes and the physical position on the chromosomes. So, for example SNP_01 is located at the nucleotide (or 'base') positioned physically at nucleotide 433,086 of chromosome 2, which has a physical size from 0 to 23.17 Mb (i.e. 23,174,626 bases). Likewise, SNP_12 is located at the nucleotide (or 'base') positioned at 26,833,907 of chromosome 6, which chromosome has a physical size from 0 to 29.07 Mb (i.e. 29,076,228 bases).

"Physical distance" between loci (e.g. between molecular markers and/or between phenotypic markers) on the same chromosome is the actually physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In cucumber, wild or primitive cucumber accessions (e.g. landraces) or wild relatives of cultivated cucumber can be used to introgress fragments of the wild genome into the genome of cultivated cucumber, *Cucumis sativus* var. *sativus* L. Such a cultivated cucumber plant thus has a "genome of cultivated *Cucumis sativus* var. *sativus*", but comprises in the genome a fragment of a wild or primitive cucumber (e.g. a landrace) or of a wild relative of cucumber, e.g. an introgression fragment of a related wild *Cucumis sativus* genome, such as *Cucumis sativus* var. *hardwickii*, *C. sativus* var. *sikkimensis Cucumis sativus* var. *xishuangbannesis*, or another wild cucumber or wild relative of cucumber. So, for example, a cultivated cucumber is provided herein comprising a genome of cultivated cucumber, and in that genome one or two introgression fragments on chromosome 2 and/or 6 of cultivated cucumber which confer enhanced yield compared to the cultivated cucumber genome lacking the introgression fragments (and having a chromosomes 2 and/or 6 of cultivated cucumber, without introgressions). It is understood that the term "introgression fragment" never includes a whole chromosome, but only a part of a chromosome. The introgression fragment can be large, e.g. even three quarter or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

"Cultivated cucumber" or "domesticated cucumber" refers to plants of *Cucumis sativus* var. *sativus* i.e. varieties, breeding lines or cultivars, cultivated by humans and having good agronomic characteristics, especially producing edible and marketable fruits of good size and quality and uniformity; such plants are not "wild cucumber" or "primitive cucumber" plants, i.e. plants which generally have much poorer yields and poorer agronomic characteristics than cultivated plants and are less uniform genetically and in their physiological and/or morphological characteristics. "Wild plants" include for example ecotypes, landraces or wild accessions or wild relatives of a species. Cultivated cucumber plants (lines or varieties) can also be distinguished from wild or primitive cucumber accessions by the significantly lower amount of SNPs (less than 2,000,000 SNPs) and INDELs (insertions/deletions of shorter than 5 bp; less than 150,000 INDELs) in the genome and their significantly lower nucleotide diversity (equal to or less than $2.3 \times 10^{-3} \pi$), as described in Table 1 of Qi et al, Nature Genetics December 2013, Vol 45, No. 12, pages 1510-1518. SNP numbers, INDEL numbers and nucleotide diversity can be determined as described herein, especially in the section 'Online Methods'.

"Indian cucumber group" refers to wild or wild relatives of cucumbers from India, having a high amount of SNPs (more than 3,000,000 SNPs) and INDELs (insertions/deletions of shorter than 5 bp; more than 200,000 INDELs) in the genome and high nucleotide diversity (more than $3.0 \times 10^{-3} \pi$ or even more than $4.0 \times 10^{-3} \pi$)

"Eurasian cucumber group" refers to cultivated cucumbers from central or western Asia, Europe and the United States, having a low amount of SNPs (less than 2,000,000 SNPs, or less than 1,500,000 SNPs) and INDELs (insertions/deletions of shorter than 5 bp; less than 150,000 INDELs) in the genome and a low nucleotide diversity (equal to or less than $2.3 \times 10^{-3} \pi$, preferably less than $2.0 \times 10^{-3} \pi$).

"East Asian cucumber group" refers to cultivated cucumbers from East Asia, such as China, Korea and Japan, having a low amount of SNPs (less than 2,000,000 SNPs, or less than 1,500,000 SNPs) and INDELs (insertions/deletions of shorter than 5 bp; less than 150,000 INDELs, preferably less than 100,000) in the genome and a low nucleotide diversity (equal to or less than $2.3 \times 10^{-3} \pi$, preferably less than $2.0 \times 10^{-3} \pi$ or even less than $1.5 \times 10^{-3} \pi$).

"Xishuangbanna cucumber group" refers to cucumbers from the Xishuangbanna region of China, having a low amount of SNPs (less than 2,000,000 SNPs, or less than 1,500,000 SNPs or even less than 100,000 SNPs) and INDELs (insertions/deletions of shorter than 5 bp; less than 150,000 INDELs, preferably less than 100,000) in the genome and a low nucleotide diversity (equal to or less than $2.3 \times 10^{-3} \pi$, preferably less than $2.0 \times 10^{-3} \pi$ or even less than $1.5 \times 10^{-3} \pi$).

"Wild cucumber" or "primitive cucumber" refers to *C. sativus* var. *sativus* which generally have much poorer yields and poorer agronomic characteristics than cultivated plants and are less uniform genetically and in their physiological and/or morphological characteristics. Wild plants include for example ecotypes, landraces or wild accessions or wild relatives of a species.

"Wild relatives of cucumber" refer to *Cucumis sativus* var. *hardwickii*, *C. sativus* var. *sikkimensis*, *Cucumis sativus* var. *xishuangbannesis*.

"Landrace(s)" refers to primitive cultivars of *Cucumis sativus* var. *sativus* developed in local geographic regions, which often show a high degree of genetic variation in their genome and exhibit a high degree of morphological and/or physiological variation within the landrace (e.g. large variation in fruit size, etc.), i.e. are significantly less uniform than cultivated cucumber. Landraces are, therefore, herein included in the group "wild cucumber", which is distinct from "cultivated cucumber".

"Uniformity" or "uniform" relates to the genetic and phenotypic characteristics of a plant line or variety. Inbred lines are genetically highly uniform as they are produced by several generations of inbreeding. Likewise, and the F1 hybrids which are produced from such inbred lines are highly uniform in their genotypic and phenotypic characteristics and performance.

The term "yield-allele" refers to an allele found at the yield locus QTL2.1 or QTL6.1 introgressed into cultivated cucumber (onto cultivated *C. sativus* var. *sativus* chromosome 2 and/or 6) from a wild cucumber or wild relative of cucumber. The term "yield-allele", thus, also encompasses yield-alleles obtainable from other *Cucumis* accessions. When one or two yield-alleles are present at the locus in the genome (i.e. in heterozygous or homozygous form), the plant line or variety produces a significantly higher fruit yield than the genetic control lacking the QTL. In cultivated cucumber plant lacking the introgression fragment, the *C. sativus* var. *sativus* allele found at the same locus on chromosome 2 and/or 6 is herein referred to as "wild type" allele (wt). As the yield QTLs are dominant, wt/wt plants show a normal yield, whereas QTL2.1/wt and/or QTL6.1/wt plants and QTL2.1/QTL2.1 and/or QTL6.1/QTL6.1 plants are plants which possess the enhanced yield phenotype conferred by the yield-allele(s). The genotype of the SNP markers provided herein is also indicative of the wild type or of either of the QTLs in homozygous or heterozygous form. E.g. the genotype of SNP_01 indicative of QTL2.1 is 'AG' (QTL2.1/wt) or 'GG' (QTL2.1/QTL2.1) while the genotype indicative of the wild type is 'AA' (wt/wt).

A genetic element, an introgression fragment, or a gene or allele conferring a trait (such as yield) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like, or combinations of techniques.

"Variant" or "orthologous" sequences or "variant QTL2.1 or QTL6.1" refers to yield QTLs (QTL2.1 or QTL6.1), or introgression fragment comprising these, which are derived from different wild cucumbers or wild relatives of cucumber plants than the QTL2.1 and QTL6.1 present in NCIMB42262, but which variants comprise one or more of the SNPs linked to QTL2.1 and QTL6.1 and wherein the variant genomic sequence comprises substantial sequence identity to the SEQ ID NO: comprising the SNP (any one of SEQ ID NO: 1-30), i.e. at least 85%, 90%, 95%, 98%, 99% sequence identity or more. Thus, when reference herein is made to a certain SNP genotype in a specific genomic sequence (selected from SEQ ID NO: 1 to SEQ ID NO: 30), this encompasses also the SNP genotype in variants of the genomic sequence, i.e. the SNP genotype in a genomic sequence comprising at least 85%, 90%, 95%, 98%, 99% sequence identity or more to the sequence referred to (selected from SEQ ID NO: 1 to SEQ ID NO: 30). Thus any reference herein to any one of SEQ ID NO: 1 to 30 in one aspect also encompasses a variant of any one of SEQ ID NO: 1 to 30, said variant comprising at least 85%, 90%, 95%, 98%, 99% sequence identity or more to said sequence.

When referring herein to a SNP genotype at a specific position, e.g. at nucleotide 75 of SEQ ID NO: 1, "or of a sequence comprising at least 90%, 91%, 92%, 93%, 94%, 95%, 96%, 97%, 98% or 99% sequence identity to the SEQ ID NO", this means that the SNP genotype is present in a variant sequence at a nucleotide corresponding to the same nucleotide (e.g. corresponding to nucleotide 75 of SEQ ID NO: 1) in the variant sequence, i.e. in a sequence comprising at least 90%, 91%, 92%, 93%, 94%, 95%, 96%, 97%, 98% or 99% sequence identity to the mentioned SEQ ID NO. It may for example be that the variant sequence is one or a few nucleotides shorter, but when one pairwise aligns the variant sequence with the mentioned SEQ ID NO, one can see which nucleotide of the variant sequence corresponds to the same nucleotide. In the variant sequence this may for example be nucleotide number 76 or 74 of that variant sequence which corresponds to nucleotide 75 of the mentioned sequence.

"Yield" or "fruit yield" or "average yield" refers to the average number of fruits (of equal to or above 1.5 cm diameter) per plant (FrPP) and/or the average fruit weight (grams) (of fruits which are equal to or above 1.5 cm diameter) per plant (GrPP) at a single harvest time-point. The single harvest time-point is in line with growers practice and chosen to maximize the number of fruits having a diameter between 1.5 cm and 5.0 cm. Depending on the desired fruit size, the time-point is generally reached when about 5%, about 10%, about 15% or about 20% of the fruits are oversized, (i.e. have a fruit diameter of 5.0 cm or more). Harvest is either by hand or by machine harvest. Thus, in one aspect all fruits per plant are harvested and only the ones with a diameter of at least 1.5 cm are counted and/or weighed (i.e. all fruits with a diameter of at least 1.5 cm are counted and/or weighed, including oversized fruits). This is done for each plant line or variety grown under the same conditions and the average FrPP and/or GrPP of each line or variety is calculated.

An "increased fruit yield" or a "significantly increased fruit yield" refers to a cultivated cucumber plant line or variety comprising an introgression fragment on chromosome 2, comprising QTL2.1, and/or comprising an introgression fragment on chromosome 6, comprising QTL6.1, having (due to the QTL) a statistically significantly higher average number of fruits per plant (FrPP) and/or a significantly higher average fruit weight per plant (GrPP) compared to the genetic control plant lacking the introgression fragments on chromosome 2 and 6 when grown in yield experiments under the same environmental conditions. Preferably field trials are carried out in several replicates (2, 3, or more) in several locations (2, 3, or more), with sufficient plants (e.g. at least 10, 15, 20, 30, 40, or more plants per line) comprising the introgression(s) and lacking the introgression(s) (i.e. genetic controls).

"Genetic control" is a cucumber line, variety or hybrid which has the same or very similar cultivated genome as the cucumber plant comprising the introgression on chromosome 2 and/or 6, except that it lacks the introgressions on chromosome 2 and 6, i.e. chromosomes 2 and 6 are "wild type", i.e. cultivated cucumber genome. For example, seeds deposited under accession number NCIMB42262 are seeds of a test-hybrid made between an introgression line comprising QTL2.1 and QTL6.1 on chromosome 2 and 6 and an elite breeding line, while the genetic control, deposited under NCIMB 42261, are seeds of the recurrent parent of the introgression line (lacking QTL2.1 and QTL6.1) and the same elite breeding line.

The term "marker assay" refers to a molecular marker assay which can be used to test whether on cultivated *C. sativus* var. *sativus* chromosome 2 and/or 6 an introgression from a wild cucumber, or from a wild relative of cucumber, is present which introgression fragment comprises the yield QTL (QTL2.1 and/or QTL6) (or whether a wild cucumber or wild relative of cucumber comprises the QTL2.1 and/or QTL6.1 in their genome), by determining the genotype of any one or more markers linked to the QTL2.1, e.g. the genotype of one or more SNP markers selected from SNP_01 to SNP_11, and/or any wild cucumber genome-specific or wild-relative of cucumber genome-specific marker in-between SNP markers SNP_01 and SNP_11, and/or within 7 cM or within 5 cM of any one of these markers, and/or within 5 Mb, 3 Mb, 2 Mb, 1 Mb, 0.5 Mb, 0.1 Mb, 50 kb, 20 kb or less of any one of these markers; and/or the genotype of any one or more markers linked to the QTL6.1, e.g. the genotype of one or more SNP markers selected from SNP_12 to SNP_30, and/or any wild cucumber genome-specific or wild-relative of cucumber genome-specific marker in-between SNP markers SNP_12 and SNP_30, and/or within 7 cM or within 5 cM of any one of these markers, and/or within 5 Mb, 3 Mb, 2 Mb, 1 Mb, 0.5 Mb, 0.1 Mb, 50 kb, 20 kb or less of any one of these markers. A marker "in between" two markers is physically located in between the markers on the chromosome.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30, 40, 50 or more plants (or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control (e.g. herein the genetic control) show a statistically significant difference in that characteristic (e.g. the p-value is less than 0.05, $p<0.05$, using ANOVA) from the (mean of the) control.

A "recombinant chromosome" refers to a chromosome having a new genetic makeup arising through crossing-over between homologous chromosomes, e.g. a "recombinant chromosome 2" or a "recombinant chromosome 6", i.e. a chromosome 2 or 6 which is not present in either of the parent plants and arose through a rare crossing-over event between homologous chromosomes of a chromosome 2 or 6 pair. Herein, for example, recombinant cucumber chromosomes 2 and 6 are provided, each comprising a yield QTL.

The term "traditional breeding techniques" encompasses herein crossing, backcrossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 2 or 6 can be obtained, identified and/or transferred.

"Backcrossing" refers to a breeding method by which a (single) trait, such as a yield QTL, can be transferred from an inferior genetic background (e.g. a wild cucumber or wild relative of cucumber; also referred to as "donor") into a superior genetic background (also referred to as "recurrent parent"), e.g. cultivated cucumber. An offspring of a cross (e.g. an F1 plant obtained by crossing a wild cucumber or wild relative of cucumber with a cultivated cucumber; or an F2 plant or F3 plant, etc., obtained from selfing the F1) is "backcrossed" to the parent with the superior genetic background, e.g. to the cultivated parent. After repeated backcrossing, the trait of the inferior genetic background will have been incorporated into the superior genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically linked to a yield QTL, can be used to detect and/or select cucumber plants comprising the yield QTL on chromosome 2 and/or 6. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination. Likewise, the closer two markers are linked to each other (e.g. within 7 cM or 5 cM, 4 cM, 3 cM, 2 cM, 1 cM or less) the less likely it is that the two markers will be separated from one another (and the more likely they will co-segregate as a unit).

A marker "within 7 cM or within 5 cM" of another marker refers to a marker which genetically maps to within the 7 cM or 5 cM region flanking the marker (i.e. either side of the marker). Similarly, a marker within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of another marker refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Cell culture" or "tissue culture" refers to the in vitro culture of cells or tissues of a plant.

"Regeneration" refers to the development of a plant from cell culture or tissue culture or vegetative propagation.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

DETAILED DESCRIPTION

The present invention relates to a cultivated *Cucumis sativus* var. *sativus* plant comprising one or two yield QTLs introgressed from wild cucumber or from a wild relative of cucumber. In particular, the increased yield is conferred by an introgression fragment on cultivated cucumber chromosome 2 and/or 6, wherein said introgression fragment is from a wild plant of the species *Cucumis sativus* var. *sativus* or from a wild relative of cucumber.

When reference is made herein to an introgression fragment on chromosome 2 or 6 having a yield QTL this encompasses various sizes of introgression fragments, e.g. the fragment as found in NCIMB42262 comprising all SNP markers (SNP_01 to SNP_11, or any marker in between these, for the fragment on chromosome 2; SNP_12 to SNP_30, or any marker in between these, for the fragment on chromosome 6), but also smaller introgression fragments (comprising e.g. 1, 2, 3 or 4 of the SNP markers), where however the fragment remains large enough to confer significantly enhanced yield (compared to the genetic control) when the introgression fragment is in heterozygous or homozygous form in the cultivated cucumber genome.

When referring to the SNP markers herein, which are indicative of the presence of the introgression fragment (and the yield QTL present on the introgression fragment), it is understood that the SNP genotype which is indicative of the introgression fragment is referred to, i.e. the SNP genotype as provided in Table 5 and Table 6 and herein below. It is noted that the SNP marker genotype can distinguish between the introgression fragment being in homozygous or heterozygous form, as shown in these Tables. In homozygous form the nucleotide is identical, while in heterozygous form the nucleotide is not identical. The SNP genotype of the 'wild type' chromosome lacking the introgression fragment is the other genotype, also listed in Table 5 and 6 (under genotype of recurrent parent). So, e.g. the genotype of SNP_01 indicative of the introgression fragment comprising QTL2.1 is 'AG' (QTL2.1/wt) or 'GG' (QTL2.1/QTL2.1) while the SNP genotype indicative of the wild type/genetic control (lacking the introgression fragment) is 'AA' (wt/wt). Thus, when referring to a plant or plant part (e.g. cell) comprising the introgression fragment in homozygous or heterozygous form, it is understood that the SNP markers linked to the introgression fragment have the corresponding SNP genotype.

So in one aspect, a cultivated *Cucumis sativus* var. *sativus* plant is provided comprising an introgression fragment on chromosome 2 and/or on chromosome 6 in homozygous or heterozygous form, wherein said introgression fragment confers an increase in cucumber fruit yield.

The QTL on chromosome 2 was mapped to the region starting at nucleotide 433,086 bp and ending at 2,958,658 bp of chromosome 2. Thus, in one aspect the introgression fragment is from a wild cucumber or a wild relative of cucumber comprises QTL2.1 or a variant thereof and comprises all of part of the region starting at nucleotide 433,086 bp and ending at 2,958,658 bp of chromosome 2.

In another aspect the introgression fragment of the invention (comprising QTL2.1 or a variant thereof) is a fragment comprising a smaller fragment (part) of the region starting at 433,086 bp and ending at 2,958,658 bp of chromosome 2, e.g. having a size of e.g. 2.5 Mb, 2 Mb, 1 Mb, 0.5 Mb, 100 kb, 50 kb, 35 kb, 30 kb, 20 kb, or less and comprising the QTL or a variant thereof. In one aspect the part is at least 5 kb, 10 kb, 20 kb in size, or more.

In one aspect the cultivated cucumber plant of the invention comprises an introgression fragment from a wild cucumber or a wild relative of cucumber, which introgression fragment comprises QTL2.1 or a variant thereof, wherein the introgression fragment comprises all of part of the region starting at 0.4 Mb and ending at 3 Mb of the physical chromosome 2; in another aspect starting at 0.3 Mb and ending at 4 Mb.

The QTL on chromosome 6 was mapped to the bottom of chromosome 6, to a region starting at nucleotide 26,833,907 bp and ending at 28,799,844 bp of chromosome 6. Thus, in one aspect the introgression fragment from a wild cucumber or a wild relative of cucumber comprises QTL6.1 or a variant thereof and comprises all of part of the region starting at nucleotide 26,833,907 bp and ending at 28,799,844 bp of chromosome 6.

In another aspect the introgression fragment of the invention (comprising QTL6.1 or a variant thereof) is a fragment comprising a smaller fragment (part) of the region starting at 26,833,907 bp and ending at 28,799,844 bp of chromosome 6, e.g. having a size of e.g. 1.9 Mb, 1 Mb, 0.5 Mb, 100 kb, 50 kb, 35 kb, 30 kb, 20 kb, or less and comprising the QTL or a variant thereof. In one aspect the part is at least 5 kb, 10 kb, 20 kb in size, or more.

In one aspect the cultivated cucumber plant of the invention comprises an introgression fragment from a wild cucumber or a wild relative of cucumber, which introgression fragment comprises QTL6.1 or a variant thereof, wherein the introgression fragment comprises all of part of the region starting at 26 Mb and ending at the end of the physical chromosome 6, i.e. at 29.07 Mb; in another aspect starting at 25 Mb and ending at the end of chromosome 6.

The increase in cucumber fruit yield is phenotypically expressed as a (statistically) significantly higher average number of fruits per plant (FrPP) of the cultivated cucumber plant line or variety comprising the introgression fragment on chromosome 2 and/or 6 in homozygous or heterozygous form compared to the genetic control line or variety lacking the introgression fragment on chromosome 2 and 6 when grown under the same environment and/or a significantly higher average fruit weight per plant (GrPP) of the plant line or variety comprising the introgression fragment compared to the genetic control line or variety lacking the introgression fragment when grown under the same environment.

Thus, different cultivated cucumber plants are provided herein, which either comprise an introgression fragment on chromosome 2 (comprising QTL2.1) in homozygous or heterozygous form; or which comprise an introgression fragment on chromosome 6 (comprising QTL6.1) in homozygous or heterozygous form; or which comprise both introgression fragments (QTL2.1 and QTL6.1), either one being in homozygous or in heterozygous form.

The plants of the invention therefore comprise a genome of cultivated cucumber, with one, two, three or four recombinant chromosomes, namely one or two recombinant chromosomes 2 and/or one or two recombinant chromosomes 6. The recombinant chromosomes comprise a fragment of a wild cucumber (or wild relative of cucumber), which is easily distinguishable from the cultivated cucumber genome by molecular marker analysis, whole genome sequencing, chromosome painting and similar techniques.

In one aspect the presence of the introgression fragment on chromosomes 2 and/or 6 in the genome of the plant or plant cell or plant tissue (or in the DNA extracted therefrom) is detectable by a molecular marker assay which detects one or more molecular markers of the introgression fragment. However, as mentioned, other techniques may be used, e.g. the SNP genotype of the markers may also be determined by sequencing or by using alternative markers located in between the SNP markers provided herein or within 7 cM, or within 5 cM, of a marker provided herein; or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of a marker provided herein.

Cucumber Plants Comprising an Introgression Fragment on Chromosome 2 (Yield QTL 2.1)

In one aspect the introgression fragment on chromosome 2 is detectable by a molecular marker assay which detects at least 1, preferably at least 2 or 3, or at least 4, 5, 6, 7, 8, 9, 10, 11 of the markers selected from the group consisting of:
a) the AG or GG genotype for the Single Nucleotide Polymorphism marker SNP_01 in SEQ ID NO: 1;
b) the AG or GG genotype for the Single Nucleotide Polymorphism marker SNP_02 in SEQ ID NO: 2;
c) the AG or GG genotype for the Single Nucleotide Polymorphism marker SNP_03 in SEQ ID NO: 3;
d) the GT or GG genotype for the Single Nucleotide Polymorphism marker SNP_04 in SEQ ID NO: 4;
e) the AC or CC genotype for the Single Nucleotide Polymorphism marker SNP_05 in SEQ ID NO: 5;
f) the CT or TT genotype for the Single Nucleotide Polymorphism marker SNP_06 in SEQ ID NO: 6;
g) the AG or GG genotype for the Single Nucleotide Polymorphism marker SNP_07 in SEQ ID NO: 7;
h) the CT or TT genotype for the Single Nucleotide Polymorphism marker SNP_08 in SEQ ID NO: 8;
i) the CT or CC genotype for the Single Nucleotide Polymorphism marker SNP_09 in SEQ ID NO: 9;
j) the GT or GG genotype for the Single Nucleotide Polymorphism marker SNP_10 in SEQ ID NO: 10;
k) the AG or AA genotype for the Single Nucleotide Polymorphism marker SNP_11 in SEQ ID NO: 11;
l) any wild cucumber genome-specific or wild-relative of cucumber genome-specific marker in between marker SNP_01 and SNP_11.

As mentioned, the skilled person can also develop other molecular markers, e.g. a wild cucumber genome specific marker or a wild-relative of cucumber genome-specific marker in-between marker SNP_01 and SNP_1 and/or within 7 cM or within 5 cM of any one of SNP_01 to SNP_11, and/or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of any one of SNP_01 to SNP_11. Such markers may also be a stretch of nucleotide, CAPS markers, INDELs, etc. The skilled person can, for example, sequence the introgression fragment found in seeds deposited under accession number NCIMB42262 and use the sequence information to develop new markers and marker assays.

In another aspect the introgression fragment on chromosome 2 is detectable by a molecular marker assay which detects at least 1, preferably at least 2 or 3, or at least 4, 5, 6, 7, 8, 9, 10, or all 11 of the markers selected from the group consisting of:
a) the AG or GG genotype for the Single Nucleotide Polymorphism marker SNP_01 in SEQ ID NO: 1;
b) the AG or GG genotype for the Single Nucleotide Polymorphism marker SNP_02 in SEQ ID NO: 2;
c) the AG or GG genotype for the Single Nucleotide Polymorphism marker SNP_03 in SEQ ID NO: 3;
d) the GT or GG genotype for the Single Nucleotide Polymorphism marker SNP_04 in SEQ ID NO: 4;
e) the AC or CC genotype for the Single Nucleotide Polymorphism marker SNP_05 in SEQ ID NO: 5;
f) the CT or TT genotype for the Single Nucleotide Polymorphism marker SNP_06 in SEQ ID NO: 6;
g) the AG or GG genotype for the Single Nucleotide Polymorphism marker SNP_07 in SEQ ID NO: 7;
h) the CT or TT genotype for the Single Nucleotide Polymorphism marker SNP_08 in SEQ ID NO: 8;
i) the CT or CC genotype for the Single Nucleotide Polymorphism marker SNP_09 in SEQ ID NO: 9;
j) the GT or GG genotype for the Single Nucleotide Polymorphism marker SNP_10 in SEQ ID NO: 10;
k) the AG or AA genotype for the Single Nucleotide Polymorphism marker SNP_11 in SEQ ID NO: 11.

In another aspect a cultivated *Cucumis sativus* var. *sativus* plant is provided comprising an introgression fragment on chromosome 2 in homozygous or heterozygous form, wherein said introgression fragment confers an increase in cucumber fruit yield and wherein said introgression fragment is detectable by a molecular marker assay which detects at least 2, 3 or 4 (or at least 5, 6, 7, 8, 9, 10 or 11) consecutive markers selected from the group consisting of:
a) the AG or GG genotype for the Single Nucleotide Polymorphism marker SNP_01 in SEQ ID NO: 1;
b) the AG or GG genotype for the Single Nucleotide Polymorphism marker SNP_02 in SEQ ID NO: 2;
c) the AG or GG genotype for the Single Nucleotide Polymorphism marker SNP_03 in SEQ ID NO: 3;
d) the GT or GG genotype for the Single Nucleotide Polymorphism marker SNP_04 in SEQ ID NO: 4;
e) the AC or CC genotype for the Single Nucleotide Polymorphism marker SNP_05 in SEQ ID NO: 5;
f) the CT or TT genotype for the Single Nucleotide Polymorphism marker SNP_06 in SEQ ID NO: 6;
g) the AG or GG genotype for the Single Nucleotide Polymorphism marker SNP_07 in SEQ ID NO: 7;
h) the CT or TT genotype for the Single Nucleotide Polymorphism marker SNP_08 in SEQ ID NO: 8;

i) the CT or CC genotype for the Single Nucleotide Polymorphism marker SNP_09 in SEQ ID NO: 9;

j) the GT or GG genotype for the Single Nucleotide Polymorphism marker SNP_10 in SEQ ID NO: 10;

k) the AG or AA genotype for the Single Nucleotide Polymorphism marker SNP_11 in SEQ ID NO: 11;

The SNP markers SNP_01 to SNP_11 are located in the given order on the introgression fragment. Consecutive markers refers to markers in the same consecutive order, so e.g. two consecutive markers may be SNP_01 and SNP_02; SNP_02 and SNP_03; SNP_03 and SNP_04, etc. and three consecutive markers may be SNP_01 and SNP_02 and SNP_03; SNP_02 and SNP_03 and SNP_04; etc.

The fragment may, thus, be smaller and lack 1, 2, 3, 4, 5, 6, 7, 8, 9 or even 10 of the markers, but it may still confer enhanced yield on the cultivated cucumber plant, i.e. it can still comprise the yield allele. Such smaller introgression fragments are an embodiment of the invention. Plants having smaller introgression fragments can be generated e.g. by starting with a plant comprising the introgression fragment as found in seeds deposited under accession number NCIMB NCIMB42262 and crossing such a plant with another cultivated cucumber plant and selfing the progeny of said cross to generate a population of plants which may contain recombinants having a smaller introgression fragment on chromosome 2. Marker assays can be used to determine the size of the smaller introgression fragment. One or more of SNP markers SNP_01 to SNP_11 may be missing (i.e. the plant may only comprise 1, 2, 3, 4, 5, 6, 7, 8, 9 or 10 of the SNP markers). The yield of plants comprising such a smaller introgression fragment can then be compared in yield experiments as described herein, i.e. growing a plurality of plants comprising the smaller introgression fragment in field experiments together with suitable control plants, lacking the introgression fragment. The control plants are preferably a genetic control. If the average yield remains significantly higher than in the control, then the smaller introgression fragment has retained the QTL2.1.

Alternatively, the same or variant QTL (QTL2.1 or variant QTL2.1) may be introgressed from a different wild source, whereby optionally not all SNP markers disclosed herein may be present. Such alternative wild sources can be identified using the SNP markers provided herein, by screening wild germplasm using a marker assay to detect the genotype of markers SNP_01 to SNP_11. Plants comprising the same or variant QTL2.1 from other sources are also an embodiment of the invention. As long as at least 1, 2, 3, 4, 5, 6, 7, 8, 9, 10 or more of the SNPs, preferably at least 2, 3, 4, 5, 6, 7, 8, 9, 10 or more consecutive SNP markers of SNP_01 to SNP_11 also have the yield-increasing genotype, the plant comprises QTL2.1 (or a variant thereof). The skilled person can introgress the QTL2.1 (or a variant thereof) into cultivated cucumber in order to enhance fruit yield as described herein.

In a specific embodiment the plant of the invention comprises an introgression fragment comprising at least a subset of SNP markers, i.e. at least 1, 2, 3, 4, or all 5 of the following markers selected from the group consisting of:

a) the AG or GG genotype for the Single Nucleotide Polymorphism marker SNP_02 in SEQ ID NO: 2;

b) the AC or CC genotype for the Single Nucleotide Polymorphism marker SNP_05 in SEQ ID NO: 5;

c) the AG or GG genotype for the Single Nucleotide Polymorphism marker SNP_07 in SEQ ID NO: 7;

d) the CT or CC genotype for the Single Nucleotide Polymorphism marker SNP_09 in SEQ ID NO: 9; and e) the GT or GG genotype for the Single Nucleotide Polymorphism marker SNP_10 in SEQ ID NO: 10.

Thus, the introgression fragment (and a cultivated cucumber plant or plant part, e.g., a cell, comprising the introgression fragment) can be detected in a marker assay by detecting the SNP genotype of the introgression fragment (i.e. of the wild cucumber or wild relative of cucumber germplasm) of one or more or all of the markers above.

In yet another aspect, the plant of the invention comprises an introgression fragment comprising at least SNP_06, i.e. the introgression fragment is detected in a marker assay detecting the CT or TT genotype for the Single Nucleotide Polymorphism marker SNP_06 in SEQ ID NO: 6. Optionally also the flanking markers, SNP_05 and/or SNP_07 are detected, i.e. the introgression fragment is detected in a marker assay detecting at least SNP_06 and optionally also at least one of the following markers:

the AC or CC genotype for the Single Nucleotide Polymorphism marker SNP_05 in SEQ ID NO: 5; and/or the AG or GG genotype for the Single Nucleotide Polymorphism marker SNP_07 in SEQ ID NO: 7; and optionally any wild cucumber genome-specific or wild-relative of cucumber genome-specific marker between SNP_05 and SNP_07.

Cucumber Plants Comprising an Introgression Fragment on Chromosome 6 (Yield QTL 6.1)

In one aspect the introgression fragment (and the cultivated cucumber plant or plant part comprising the introgression fragment) on chromosome 6 is detectable by a molecular marker assay which detects at least 1, preferably at least 2 or 3, or at least 4, 5, 6, 7, 8, 9, 10, 11, 12, 13, 14, 15, 16, 17, 18, or 19 of the markers selected from the group consisting of:

a) the AG or AA genotype for the Single Nucleotide Polymorphism marker SNP_12 in SEQ ID NO: 12;

b) the AG or AA genotype for the Single Nucleotide Polymorphism marker SNP_13 in SEQ ID NO: 13;

c) the AG or GG genotype for the Single Nucleotide Polymorphism marker SNP_14 in SEQ ID NO: 14;

d) the CT or TT genotype for the Single Nucleotide Polymorphism marker SNP_15 in SEQ ID NO: 15;

e) the AG or AA genotype for the Single Nucleotide Polymorphism marker SNP_16 in SEQ ID NO: 16;

f) the CT or TT genotype for the Single Nucleotide Polymorphism marker SNP_17 in SEQ ID NO: 17;

g) the CT or CC genotype for the Single Nucleotide Polymorphism marker SNP_18 in SEQ ID NO: 18;

h) the AC or AA genotype for the Single Nucleotide Polymorphism marker SNP_19 in SEQ ID NO: 19;

i) the AC or AA genotype for the Single Nucleotide Polymorphism marker SNP_20 in SEQ ID NO: 20;

j) the AG or GG genotype for the Single Nucleotide Polymorphism marker SNP_21 in SEQ ID NO: 21;

k) the CT or CC genotype for the Single Nucleotide Polymorphism marker SNP_22 in SEQ ID NO: 22;

l) the AG or AA genotype for the Single Nucleotide Polymorphism marker SNP_23 in SEQ ID NO: 23;

m) the CT or CC genotype for the Single Nucleotide Polymorphism marker SNP_24 in SEQ ID NO: 24;

n) the AG or GG genotype for the Single Nucleotide Polymorphism marker SNP_25 in SEQ ID NO: 25;

o) the CT or CC genotype for the Single Nucleotide Polymorphism marker SNP_26 in SEQ ID NO: 26;

p) the AG or AA genotype for the Single Nucleotide Polymorphism marker SNP_27 in SEQ ID NO: 27;

q) the CT or CC genotype for the Single Nucleotide Polymorphism marker SNP_28 in SEQ ID NO: 28;
r) the CT or CC genotype for the Single Nucleotide Polymorphism marker SNP_29 in SEQ ID NO: 29;
s) the GT or TT genotype for the Single Nucleotide Polymorphism marker SNP_30 in SEQ ID NO: 30;
t) any wild cucumber genome-specific or wild-relative of cucumber genome-specific marker in between marker SNP_12 and SNP_30.

As mentioned, the skilled person can also develop other molecular markers, e.g. a wild cucumber genome specific marker or wild-relative of cucumber genome-specific marker in between marker SNP_12 and SNP_30 and/or within 7 cM or within 5 cM of any one of SNP_12 to SNP_30, and/or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of any one of SNP_12 to SNP_30. Such markers may also be a stretch of nucleotide, CAPS markers, INDELs, etc. The skilled person can, for example, sequence the introgression fragment found in seeds deposited under accession number NCIMB42262 and use the sequence information to develop new markers and marker assays.

In another aspect the introgression fragment on chromosome 6 is detectable by a molecular marker assay which detects at least 1, preferably at least 2 or 3, or at least 4, 5, 6, 7, 8, 9, 10, 11, 12, 13, 14, 15, 16, 17, 18 or all 19 of the markers selected from the group consisting of:
a) the AG or AA genotype for the Single Nucleotide Polymorphism marker SNP_12 in SEQ ID NO: 12;
b) the AG or AA genotype for the Single Nucleotide Polymorphism marker SNP_13 in SEQ ID NO: 13;
c) the AG or GG genotype for the Single Nucleotide Polymorphism marker SNP_14 in SEQ ID NO: 14;
d) the CT or TT genotype for the Single Nucleotide Polymorphism marker SNP_15 in SEQ ID NO: 15;
e) the AG or AA genotype for the Single Nucleotide Polymorphism marker SNP_16 in SEQ ID NO: 16;
f) the CT or TT genotype for the Single Nucleotide Polymorphism marker SNP_17 in SEQ ID NO: 17;
g) the CT or CC genotype for the Single Nucleotide Polymorphism marker SNP_18 in SEQ ID NO: 18;
h) the AC or AA genotype for the Single Nucleotide Polymorphism marker SNP_19 in SEQ ID NO: 19;
i) the AC or AA genotype for the Single Nucleotide Polymorphism marker SNP_20 in SEQ ID NO: 20;
j) the AG or GG genotype for the Single Nucleotide Polymorphism marker SNP_21 in SEQ ID NO: 21;
k) the CT or CC genotype for the Single Nucleotide Polymorphism marker SNP_22 in SEQ ID NO: 22;
l) the AG or AA genotype for the Single Nucleotide Polymorphism marker SNP_23 in SEQ ID NO: 23;
m) the CT or CC genotype for the Single Nucleotide Polymorphism marker SNP_24 in SEQ ID NO: 24;
n) the AG or GG genotype for the Single Nucleotide Polymorphism marker SNP_25 in SEQ ID NO: 25;
o) the CT or CC genotype for the Single Nucleotide Polymorphism marker SNP_26 in SEQ ID NO: 26;
p) the AG or AA genotype for the Single Nucleotide Polymorphism marker SNP_27 in SEQ ID NO: 27;
q) the CT or CC genotype for the Single Nucleotide Polymorphism marker SNP_28 in SEQ ID NO: 28;
r) the CT or CC genotype for the Single Nucleotide Polymorphism marker SNP_29 in SEQ ID NO: 29;
s) the GT or TT genotype for the Single Nucleotide Polymorphism marker SNP_30 in SEQ ID NO: 30;

In another aspect a cultivated Cucumis sativus var. sativus plant is provided comprising an introgression fragment on chromosome 6 in homozygous or heterozygous form, wherein said introgression fragment confers an increase in cucumber fruit yield and wherein said introgression fragment is detectable by a molecular marker assay which detects at least 2, 3 or 4 (or at least 5, 6, 7, 8, 9, 10, 11, 12, 13, 14, 15, 16, 17, 18 or 19) consecutive markers selected from the group consisting of:
a) the AG or AA genotype for the Single Nucleotide Polymorphism marker SNP_12 in SEQ ID NO: 12;
b) the AG or AA genotype for the Single Nucleotide Polymorphism marker SNP_13 in SEQ ID NO: 13;
c) the AG or GG genotype for the Single Nucleotide Polymorphism marker SNP_14 in SEQ ID NO: 14;
d) the CT or TT genotype for the Single Nucleotide Polymorphism marker SNP_15 in SEQ ID NO: 15;
e) the AG or AA genotype for the Single Nucleotide Polymorphism marker SNP_16 in SEQ ID NO: 16;
f) the CT or TT genotype for the Single Nucleotide Polymorphism marker SNP_17 in SEQ ID NO: 17;
g) the CT or CC genotype for the Single Nucleotide Polymorphism marker SNP_18 in SEQ ID NO: 18;
h) the AC or AA genotype for the Single Nucleotide Polymorphism marker SNP_19 in SEQ ID NO: 19;
i) the AC or AA genotype for the Single Nucleotide Polymorphism marker SNP_20 in SEQ ID NO: 20;
j) the AG or GG genotype for the Single Nucleotide Polymorphism marker SNP_21 in SEQ ID NO: 21;
k) the CT or CC genotype for the Single Nucleotide Polymorphism marker SNP_22 in SEQ ID NO: 22;
l) the AG or AA genotype for the Single Nucleotide Polymorphism marker SNP_23 in SEQ ID NO: 23;
m) the CT or CC genotype for the Single Nucleotide Polymorphism marker SNP_24 in SEQ ID NO: 24;
n) the AG or GG genotype for the Single Nucleotide Polymorphism marker SNP_25 in SEQ ID NO: 25;
o) the CT or CC genotype for the Single Nucleotide Polymorphism marker SNP_26 in SEQ ID NO: 26;
p) the AG or AA genotype for the Single Nucleotide Polymorphism marker SNP_27 in SEQ ID NO: 27;
q) the CT or CC genotype for the Single Nucleotide Polymorphism marker SNP_28 in SEQ ID NO: 28;
r) the CT or CC genotype for the Single Nucleotide Polymorphism marker SNP_29 in SEQ ID NO: 29; and
s) the GT or TT genotype for the Single Nucleotide Polymorphism marker SNP_30 in SEQ ID NO: 30.

The SNP markers SNP_12 to SNP_30 are located in the given order on the introgression fragment. Consecutive markers refers to markers in the same consecutive order, so e.g. two consecutive markers may be SNP_12 and SNP_13; SNP_13 and SNP_14; SNP_14 and SNP_15; etc. and three consecutive markers may be SNP_12 and SNP_13 and SNP_14; SNP_13 and SNP_14 and SNP_15; etc.

The fragment may, thus, be smaller and lack 1, 2, 3, 4, 5, 6, 7, 8, 9, 10, 11, 12, 13, 14, 15, 16, 17 or even 18 of the markers, but it may still confer enhanced yield on the cultivated cucumber plant, i.e. it can still comprise the yield allele. Such smaller introgression fragments are an embodiment of the invention. Plants having smaller introgression fragments can be generated e.g. by starting with a plant comprising the introgression fragment as found in seeds deposited under accession number NCIMB42262 and crossing such a plant with another cultivated cucumber plant and selfing the progeny of said cross to generate a population of plants which may contain recombinants having a smaller introgression fragment on chromosome 6. Marker assays can be used to determine the size of the smaller introgression fragment. One or more of SNP markers SNP_12 to SNP_30 may be missing (i.e. the plant may only comprise 1, 2, 3, 4, 5, 6, 7, 8, 9, 10, 11, 12, 13, 14, 15, 16, 17 or 18 of the SNP markers). The yield of plants comprising such a smaller introgression fragment can then be compared in yield experiments as described herein, i.e. growing a plurality of plants comprising the smaller introgression fragment in field experiments together with suitable control plants, lacking the introgression fragment. The control plants are preferably a genetic control. If the average yield remains significantly higher than in the control, then the smaller introgression fragment has retained the QTL6.1.

Alternatively, the same or variant QTL (QTL6.1 or variant QTL6.1) may be introgressed from a different wild source, whereby optionally not all SNP markers disclosed herein may be present. Such alternative wild sources can be identified using the SNP markers provided herein, by screening wild germplasm using a marker assay to detect the genotype of markers SNP_12 to SNP_30. Plants comprising the QTL6.1 or variant QTL6.1 from other sources are also an embodiment of the invention. As long as at least 1, 2, 3, 4, 5, 6, 7, 8, 9, 10, 11, 12, 13, 14, 15, 16, 17, 18 or more of the SNPs, preferably at least 2, 3, 4, 5, 6, 7, 8, 9, 10, 11, 12, 13, 14, 15, 16, 17, 18 or more consecutive SNP markers of SNP_12 to SNP_30 also have the yield-increasing genotype, the plant comprises QTL6.1 (or a variant thereof). The skilled person can introgress the QTL6.1 (or a variant thereof) into cultivated cucumber in order to enhance fruit yield as described herein.

In a specific embodiment the plant of the invention comprises an introgression fragment comprising at least a subset of SNP markers, i.e. at least 1, 2, 3, 4, 5, 6, 7, 8, 9, 10, 11, 12 or all 13 of the following markers selected from the group consisting of:

the AG or AA genotype for the Single Nucleotide Polymorphism marker SNP_12 in SEQ ID NO: 12;
the AG or AA genotype for the Single Nucleotide Polymorphism marker SNP_13 in SEQ ID NO: 13;
the CT or CC genotype for the Single Nucleotide Polymorphism marker SNP_18 in SEQ ID NO: 18;
the AC or AA genotype for the Single Nucleotide Polymorphism marker SNP_19 in SEQ ID NO: 19;
the AC or AA genotype for the Single Nucleotide Polymorphism marker SNP_20 in SEQ ID NO: 20;
the AG or GG genotype for the Single Nucleotide Polymorphism marker SNP_21 in SEQ ID NO: 21;
the CT or CC genotype for the Single Nucleotide Polymorphism marker SNP_22 in SEQ ID NO: 22;
the AG or AA genotype for the Single Nucleotide Polymorphism marker SNP_23 in SEQ ID NO: 23;
the CT or CC genotype for the Single Nucleotide Polymorphism marker SNP_24 in SEQ ID NO: 24;
the AG or GG genotype for the Single Nucleotide Polymorphism marker SNP_25 in SEQ ID NO: 25;
the CT or CC genotype for the Single Nucleotide Polymorphism marker SNP_26 in SEQ ID NO: 26;
the CT or CC genotype for the Single Nucleotide Polymorphism marker SNP_28 in SEQ ID NO: 28;
the GT or TT genotype for the Single Nucleotide Polymorphism marker SNP_30 in SEQ ID NO: 30.

Especially, in one aspect the cultivated cucumber plant of the invention comprises at least 1, 2 or 3 markers selected from the group consisting of:

the AG or AA genotype for the Single Nucleotide Polymorphism marker SNP_13 in SEQ ID NO: 13;
the CT or CC genotype for the Single Nucleotide Polymorphism marker SNP_18 in SEQ ID NO: 18;
the CT or CC genotype for the Single Nucleotide Polymorphism marker SNP_28 in SEQ ID NO: 28; and
optionally any wild cucumber genome-specific or wild-relative of cucumber genome-specific marker in between marker SNP_13 and SNP_18 and/or in between marker SNP_18 and SNP_28.

Thus, the introgression fragment (and a cultivated cucumber plant or plant part, e.g., a cell, comprising the introgression fragment) can be detected in a marker assay by detecting the SNP genotype of the introgression fragment (i.e. of the wild cucumber or wild relative of cucumber germplasm) of one or more or all of the markers above.

Thus, in one aspect, two Quantitative Trait Loci (QTL2.1 and QTL6.1) were found to be present on chromosome 2 and 6 of wild cucumber which, when transferred (introgressed) into a cultivated, cucumber variety or breeding line separately or in combination, and when present in heterozygous or homozygous form, confers significantly enhanced fruit yield onto the cultivated cucumber plant. The QTLs, or the introgression fragments comprising the QTLs (comprising the yield allele), are thus dominant, i.e. it is sufficient to have the introgression fragment on one of the chromosomes 2 or 6 (one recombinant chromosome 2 or 6), while the homologous chromosome 2 or 6 of the pair may be a (non-recombinant) chromosome 2 or 6 of cultivated C. sativus var. sativus lacking the introgression fragment.

Although the present sources of the two yield QTLs is a single, specific wild source, there are likely other wild Cucumis sativus accessions which comprise QTL2.1 and/or QTL6.1 at the same locus on chromosome 2 and/or 6. Such loci may comprise yield alleles which have slightly different nucleotide sequences, i.e. variants of the alleles (QTLs) found herein. Such variant QTLs can also be identified and introgressed into cultivated cucumber as described herein, to generate a cultivated cucumber plant comprising a genome of cultivated C. sativus var. sativus and a recombinant chromosome 2 and/or 6, whereby the recombinant chromosome 2 and/or 6 comprises a wild Cucumis sativus species introgression fragment, which confers an enhanced yield phenotype onto the cultivated cucumber plant when present in homozygous or heterozygous form. To identify such wild cucumber or wild relatives of cucumber comprising QTL2.1 and/or QTL6.1, wild accessions can be screened, e.g. in a marker assay or by sequence comparison or other methods, for the presence of one or more of the SNP markers provided herein. The putative yield QTLs (or variant QTLs) can then be introgressed into cultivated cucumber, e.g. using MAS, i.e. using one or more (or all) of the SNP markers provided herein to detect and/or select progeny plants (e.g. backcross plants) comprising a recombinant chromosome 2 and/or 6. The selected plants, i.e. the cultivated cucumber plants comprising an introgression fragment on chromosome 2 and/or 6 wherein the introgression fragment on chromosome 2 is detectable by one or more of the SNP markers SNP_01 to SNP_11 (as described elsewhere herein), and wherein the introgression fragment on chromosome 6 is detectable by one or more of the SNP markers SNP_12 to SNP_30 (as described elsewhere herein), can then be phenotyped in yield experiments together with the suitable control plants, preferably at least the genetic control, in order to determine whether the introgression fragment indeed causes a significant yield increase.

Accessions of wild cucumbers and wild relatives of cucumber, are obtainable from the USDA National Plant Germplasm System collection or other seed collections, and can thus be screened for the presence of QTL2.1 and/or QTL6.1 using e.g. a marker assay as described herein, and accessions comprising one or more of the SNP markers (e.g. at least 1, 2, 3, 4, 5, 6, 7, 8, 9, 10 or all 11 SNP markers indicative of QTL2.1; and/or at least 1, 2, 3, 4, 5, 6, 7, 8, 9, 10, 11, 12, 13, 14, 15, 16, 17, 18 or all 19 SNP markers indicative of QTL6.1) can be crossed with a cultivated cucumber plant having normal wild-type, non-recombinant chromosomes 2 and 6. The F2 generation (or further generation, such as the F3 or a backcross generation) can then be screened for recombinant plants having the introgression fragment or a part thereof, using the molecular marker assays described herein.

In a specific embodiment, the introgression fragment comprising the yield QTL2.1 and/or the yield QTL6.1 is derivable from (or derived from) or obtainable from (or obtained from; or as present in) seeds, a representative sample of which has been deposited under accession number NCIMB 42262, or from progeny thereof. The progeny may be any progeny which retain the one or more (or all) SNP markers indicative of the QTL, as described. Thus, progeny are not limited to F1 or F2 progeny of the deposit, but can be any progeny, whether obtained by selfing and/or crossing with another cucumber plant.

In one embodiment the introgression fragment is identifiable by one or more of the markers described elsewhere herein, especially markers SNP_01 to SNP_11 for the introgression fragment on chromosome 2 and SNP_12 to SNP_30 for the introgression fragment on chromosome 6. In one aspect the invention provides a cultivated cucumber plant, having a genome of cultivated (domesticated) cucumber which comprises enhanced fruit yield, wherein the enhanced fruit yield is conferred by an introgression fragment on the cultivated cucumber chromosome 2 and/or chromosome 6, wherein said introgression fragment is obtained by (or obtainable by) crossing a cultivated plant grown from seeds deposited under NCIMB 42262 or progeny of this plant (which comprises one or more the markers disclosed herein linked to the QTL) with a cultivated cucumber plant.

In another embodiment the invention relates to a plant of the invention i.e. a cultivated *Cucumis sativus* var. *sativus* plant comprising an introgression fragment from a wild cucumber or wild relative of cucumber on chromosome 2 and/or 6 in homozygous or heterozygous form and wherein said introgression fragment is the introgression fragment is in one aspect "as in"/is "identical to"/is "the same as in" the seeds deposited under number NCIMB 42262, or is a shorter fragment thereof, but still confers enhanced fruit yield.

In yet another embodiment the invention relates to a plant of the invention i.e. a cultivated *Cucumis sativus* var. *sativus* plant comprising an introgression fragment from a wild cucumber or wild relative of cucumber on chromosome 2 and/or 6 in homozygous or heterozygous form and wherein said introgression fragment is the introgression fragment is a variant of the introgression fragment seeds deposited under number NCIMB 42262, i.e. it comprises the yield QTL, but the genomic sequence may be different. As wild accessions will be genetically divergent, the genomic sequence of an introgression fragment comprising QTL2.1 or QTL6.1 from other wild cucumber accessions or wild relatives of cucumber will most likely not be identical to the genomic sequence as introgressed into NCIMB42262, and even the yield conferring gene (comprising a promoter, introns and exons) may be divergent in nucleotide sequence, but the function will be the same, i.e. conferring enhanced fruit yield. The divergence can be seen in that certain SNP markers linked to QTL2.1 and/or QTL6.1 may be commonly found in various accessions, while other SNP markers may only be found in specific accessions. So for example not all of SNP_01 to SNP_11 and/or SNP_12 to SNP_30 may be found in other wild cucumber plants or wild relatives of cucumber. However, the yield enhancing QTL2.1 and QTL6.1 (comprising e.g. a variant or ortholog of the yield allele) may still be present in such wild accessions. The skilled person is capable of identifying and introgressing the QTLs 2.1 and 6.1 comprising region found in other wild cucumber accessions or other wild relatives of cucumber into cultivated cucumber.

In one embodiment the presence of the introgression fragment, or the chromosome 2 region (or variant or orthologous chromosome 2 region), comprising QTL2.1, is detectable by a molecular marker assay which detects at least 1, preferably at least 2, 3, 4, 5, 6, 7, 8, 9, 10 or more (or all 11) Single Nucleotide Polymorphism (SNP) markers selected from the group consisting of:

a) the AG or GG genotype for the Single Nucleotide Polymorphism marker SNP_01 in SEQ ID NO: 1;
b) the AG or GG genotype for the Single Nucleotide Polymorphism marker SNP_02 in SEQ ID NO: 2;
c) the AG or GG genotype for the Single Nucleotide Polymorphism marker SNP_03 in SEQ ID NO: 3;
d) the GT or GG genotype for the Single Nucleotide Polymorphism marker SNP_04 in SEQ ID NO: 4;
e) the AC or CC genotype for the Single Nucleotide Polymorphism marker SNP_05 in SEQ ID NO: 5;
f) the CT or TT genotype for the Single Nucleotide Polymorphism marker SNP_06 in SEQ ID NO: 6;
g) the AG or GG genotype for the Single Nucleotide Polymorphism marker SNP_07 in SEQ ID NO: 7;
h) the CT or TT genotype for the Single Nucleotide Polymorphism marker SNP_08 in SEQ ID NO: 8;
i) the CT or CC genotype for the Single Nucleotide Polymorphism marker SNP_09 in SEQ ID NO: 9;
j) the GT or GG genotype for the Single Nucleotide Polymorphism marker SNP_10 in SEQ ID NO: 10;
k) the AG or AA genotype for the Single Nucleotide Polymorphism marker SNP_11 in SEQ ID NO: 11.

Thus, in one embodiment the plants according to the invention comprise at least a Guanine (G) (i.e. the AG or GG genotype) instead of two Adenines (AA) at nucleotide 75 of SEQ ID NO: 1 (referred to as SNP_01) or at the equivalent nucleotide of a genomic sequence comprising substantial sequence identity to SEQ ID NO:1; and/or at least a Guanine (G) (i.e. the AG or GG genotype) instead of two Adenines (AA) at nucleotide 75 of SEQ ID NO: 2 (referred to as SNP_02) or at the equivalent nucleotide of a genomic sequence comprising substantial sequence identity to SEQ ID NO:2; and/or at least a Guanine (G) (i.e. the AG or GG genotype) instead of two Adenines (AA) at nucleotide 75 of SEQ ID NO: 3 (referred to as SNP_03) or at the equivalent nucleotide of a genomic sequence comprising substantial sequence identity to SEQ ID NO:3; and/or at least a Guanine (G) (i.e. the GG or GT genotype) instead of two Thymines (TT) at nucleotide 75 of SEQ ID NO: 4 (referred to as SNP_04) or at the equivalent nucleotide of a genomic sequence comprising substantial sequence identity to SEQ ID NO:4; and/or at least a Cytosine (C) (i.e. the CC or AC genotype) instead of two Adenines (AA) at nucleotide 75 of SEQ ID NO: 5 (referred to as SNP_05) or at the equivalent nucleotide of a genomic sequence comprising substantial sequence identity to SEQ ID NO:5; and/or at least a Thymine (T) (i.e. the TT or CT genotype) instead of two Cytosines (CC) at nucleotide 75 of SEQ ID NO: 6 (referred to as SNP_06) or at the equivalent nucleotide of a genomic sequence comprising substantial sequence identity to SEQ ID NO:6; and/or at least a Guanine (G) (i.e. the GG or AG genotype) instead of two Adenines (AA) at nucleotide 75 of SEQ ID NO: 7 (referred to as SNP_07) or at the equivalent nucleotide of a genomic sequence comprising substantial sequence identity to SEQ ID NO:7; and/or at least a Thymine (T) (i.e. the TT or CT genotype) instead of two Cytosines (CC) at nucleotide 75 of SEQ ID NO: 8 (referred to as SNP_08) or at the equivalent nucleotide of a genomic sequence comprising substantial sequence identity to SEQ ID NO:8; and/or at least a Cytosine (C) (i.e. the CC or CT genotype) instead of two Thymines (TT) at nucleotide 75 of SEQ ID NO: 9 (referred to as SNP_09) or at the equivalent nucleotide of a genomic sequence comprising substantial sequence identity to SEQ ID NO:9; and/or at least a Guanine (G) (i.e. the GG or GT genotype) instead of two Thymines (TT) at nucleotide 75 of SEQ ID NO: 10 (referred to as SNP_10) or at the equivalent nucleotide of a genomic sequence comprising substantial sequence identity to SEQ ID NO: 10; and/or at least a Adenine (A) (i.e. the AA or AG genotype) instead of two Guanines (GG) at nucleotide 75 of SEQ ID NO: 11 (referred to as SNP_11) or at the equivalent nucleotide of a genomic sequence comprising substantial sequence identity to SEQ ID NO: 11.

In a further one embodiment the presence of the introgression fragment, or the chromosome 6 region (or variant or orthologous chromosome 6 region), comprising QTL6.1, is detectable by a molecular marker assay which detects at least 1, preferably at least 2, 3, 4, 5, 6, 7, 8, 9, 10, 11, 12, 13, 14, 15, 16, 17, 18 or more (or all 19) Single Nucleotide Polymorphism (SNP) markers selected from the group consisting of:

a) the AG or AA genotype for the Single Nucleotide Polymorphism marker SNP_12 in SEQ ID NO: 12;
b) the AG or AA genotype for the Single Nucleotide Polymorphism marker SNP_13 in SEQ ID NO: 13;
c) the AG or GG genotype for the Single Nucleotide Polymorphism marker SNP_14 in SEQ ID NO: 14;
d) the CT or TT genotype for the Single Nucleotide Polymorphism marker SNP_15 in SEQ ID NO: 15;
e) the AG or AA genotype for the Single Nucleotide Polymorphism marker SNP_16 in SEQ ID NO: 16;
f) the CT or TT genotype for the Single Nucleotide Polymorphism marker SNP_17 in SEQ ID NO: 17;
g) the CT or CC genotype for the Single Nucleotide Polymorphism marker SNP_18 in SEQ ID NO: 18;
h) the AC or AA genotype for the Single Nucleotide Polymorphism marker SNP_19 in SEQ ID NO: 19;
i) the AC or AA genotype for the Single Nucleotide Polymorphism marker SNP_20 in SEQ ID NO: 20;
j) the AG or GG genotype for the Single Nucleotide Polymorphism marker SNP_21 in SEQ ID NO: 21;
k) the CT or CC genotype for the Single Nucleotide Polymorphism marker SNP_22 in SEQ ID NO: 22;
l) the AG or AA genotype for the Single Nucleotide Polymorphism marker SNP_23 in SEQ ID NO: 23;
m) the CT or CC genotype for the Single Nucleotide Polymorphism marker SNP_24 in SEQ ID NO: 24;
n) the AG or GG genotype for the Single Nucleotide Polymorphism marker SNP_25 in SEQ ID NO: 25;
o) the CT or CC genotype for the Single Nucleotide Polymorphism marker SNP_26 in SEQ ID NO: 26;
p) the AG or AA genotype for the Single Nucleotide Polymorphism marker SNP_27 in SEQ ID NO: 27;
q) the CT or CC genotype for the Single Nucleotide Polymorphism marker SNP_28 in SEQ ID NO: 28;
r) the CT or CC genotype for the Single Nucleotide Polymorphism marker SNP_29 in SEQ ID NO: 29;
s) the GT or TT genotype for the Single Nucleotide Polymorphism marker SNP_30 in SEQ ID NO: 30;

Thus, in one embodiment the plants according to the invention comprise at least a Adenine (A) (i.e. the AA or AG genotype) instead of two Guanines (GG) at nucleotide 75 of SEQ ID NO: 12 (referred to as SNP_12) or at the equivalent nucleotide of a genomic sequence comprising substantial sequence identity to SEQ ID NO:12; and/or at least a Adenine (A) (i.e. the AA or AG genotype) instead of two Guanines (GG) at nucleotide 75 of SEQ ID NO: 13 (referred to as SNP_13) or at the equivalent nucleotide of a genomic sequence comprising substantial sequence identity to SEQ ID NO: 13; and/or at least a Guanine (G) (i.e. the AG or GG genotype) instead of two Adenines (AA) at nucleotide 75 of SEQ ID NO: 14 (referred to as SNP_14) or at the equivalent nucleotide of a genomic sequence comprising substantial sequence identity to SEQ ID NO: 14; and/or at least a Thymine (T) (i.e. the TT or CT genotype) instead of two Cytosines (CC) at nucleotide 75 of SEQ ID NO: 15 (referred to as SNP_15) or at the equivalent nucleotide of a genomic sequence comprising substantial sequence identity to SEQ ID NO: 15; and/or at least a Adenine (A) (i.e. the AA or AG genotype) instead of two Guanines (GG) at nucleotide 75 of SEQ ID NO: 16 (referred to as SNP_16) or at the equivalent nucleotide of a genomic sequence comprising substantial sequence identity to SEQ ID NO: 16; and/or at least a Thymine (T) (i.e. the TT or CT genotype) instead of two Cytosines (CC) at nucleotide 75 of SEQ ID NO: 17 (referred to as SNP_17) or at the equivalent nucleotide of a genomic sequence comprising substantial sequence identity to SEQ ID NO: 17; and/or at least a Cytosine (C) (i.e. the CC or CT genotype) instead of two Thymines (TT) at nucleotide 75 of SEQ ID NO: 18 (referred to as SNP_18) or at the equivalent nucleotide of a genomic sequence comprising substantial sequence identity to SEQ ID NO: 18; and/or at least a Adenine (A) (i.e. the AA or AC genotype) instead of two Cytosines (CC) at nucleotide 75 of SEQ ID NO: 19 (referred to as SNP_19) or at the equivalent nucleotide of a genomic sequence comprising substantial sequence identity to SEQ ID NO: 19; and/or at least a Adenine (A) (i.e. the AA or AC genotype) instead of two Cytosines (CC) at nucleotide 75 of SEQ ID NO: 20 (referred to as SNP_20) or at the equivalent nucleotide of a genomic sequence comprising substantial sequence identity to SEQ ID NO:20; and/or at least a Guanine (G) (i.e. the GG or AG genotype) instead of two Adenines (AA) at nucleotide 75 of SEQ ID NO: 21 (referred to as SNP_21) or at the equivalent nucleotide of a genomic sequence comprising substantial sequence identity to SEQ ID NO:21; and/or at least a Cytosine (C) (i.e. the CC or CT genotype) instead of two Thymines (TT) at nucleotide 75 of SEQ ID NO: 22 (referred to as SNP_22) or at the equivalent nucleotide of a genomic sequence comprising substantial sequence identity to SEQ ID NO:22; and/or at least a Adenine (A) (i.e. the AA or AG genotype) instead of two Guanines (GG) at nucleotide 75 of SEQ ID NO: 23 (referred to as SNP_23) or at the equivalent nucleotide of a genomic sequence comprising substantial sequence identity to SEQ ID NO:23; and/or at least a Cytosine (C) (i.e. the CC or CT genotype) instead of two Thymines (TT) at nucleotide 75 of SEQ ID NO: 24 (referred to as SNP_24) or at the equivalent nucleotide of a genomic sequence comprising substantial sequence identity to SEQ ID NO:24; and/or at least a Guanine (G) (i.e. the GG or AG genotype) instead of two Adenines (AA) at nucleotide 75 of SEQ ID NO: 25 (referred to as SNP_25) or at the equivalent nucleotide of a genomic sequence comprising substantial sequence identity to SEQ ID NO:25; and/or at least a Cytosine (C) (i.e. the CC or CT genotype) instead of two Thymines (TT) at nucleotide 75 of SEQ ID NO: 26 (referred to as SNP_26) or at the equivalent nucleotide of a genomic sequence comprising substantial sequence identity to SEQ ID NO:26; and/or at least a Adenine (A) (i.e. the AA or AG genotype) instead of two Guanines (GG) at nucleotide 75 of SEQ ID NO: 27 (referred to as SNP_27) or at the equivalent nucleotide of a genomic sequence comprising substantial sequence identity to SEQ ID NO:27; and/or at least a Cytosine (C) (i.e. the CC or CT genotype) instead of two Thymines (TT) at nucleotide 75 of SEQ ID NO: 28 (referred to as SNP_28) or at the equivalent nucleotide of a genomic sequence comprising substantial sequence identity to SEQ ID NO:28; and/or at least a Cytosine (C) (i.e. the CC or CT genotype) instead of two Thymines (TT) at nucleotide 75 of SEQ ID NO: 29 (referred to as SNP_29) or at the equivalent nucleotide of a genomic sequence comprising substantial sequence identity to SEQ ID NO:29; and/or at least a Thymine (T) (i.e. the TT or GT genotype) instead of two Guanines (GG) at nucleotide 75 of SEQ ID NO: 30 (referred to as SNP_30) or at the equivalent nucleotide of a genomic sequence comprising substantial sequence identity to SEQ ID NO:30;

The SNP genotype refers to two nucleotides, and genomic sequences comprising one of these two nucleotides, one on each chromosome 2 (for SNP_01 to SNP_11) or 6 (for SNP_12 to SNP_30). So a plant having a TT genotype for SNP_30 has an identical nucleotide (T) on both chromosomes, while a plant having an GT genotype for SNP_30 has one chromosome with an G at nucleotide 75 of SEQ ID NO: 30 (or at the equivalent nucleotide of a genomic sequence comprising substantial sequence identity to SEQ ID NO:30) and one chromosome with a T at nucleotide 75 of SEQ ID NO: 30 (or at the equivalent nucleotide of a genomic sequence comprising substantial sequence identity to SEQ ID NO:30). As the genomic sequences around the SNP markers provided herein may vary slightly in introgression fragments from other wild cucumbers or wild relatives of cucumber (i.e. variants or orthologous chromosome 2 or 6 regions) it is clear that the nucleotide sequences before and after the SNP may not be 100% identical to the sequences provided herein. Therefore sequences having substantial sequence identity to the sequences provided herein, but which comprise the same SNP, are encompassed herein.

In one aspect, the introgression fragment, or the chromosome 2 or 6 region (or variant or orthologous chromosome 2 or 6 region) comprising the QTL (QTL2.1 or variant and/or QTL6.1 or variant), which is detectable by the above one or more markers is from a wild cucumber plant or wild relative cucumber, and in one aspect it is from a plant of which a representative sample of seeds has been deposited under accession number NCIMB42262 or progeny thereof; in one aspect it is therefore the same introgression fragment as found on chromosome 2 and on chromosome 6 in seeds deposited under accession number NCIMB42262, or a smaller fragment. In one aspect the introgression fragment on chromosome 2 and/or 6 is equal to or less than 10 Mb in size, preferably equal to or less than 8 Mb in size, more preferably equal to or less than 6, 5, 4, 3 or 2.5 Mb in size, e.g. equal to or less than 2 Mb. In one aspect the introgression fragment is at least 0.2 Mb, 0.5 Mb, 1.0 Mb, 1.5 Mb, 1.9 Mb, 2.0 Mb, 2.5 Mb or 3 Mb in size. Thus, various ranges of introgression sizes are encompassed herein, such as fragments less than 10 Mb but more than 0.2 Mb, less than 5 Mb or 3 Mb but more than 0.2 Mb, 0.5 MB or 1 Mb, etc. The size can be easily determined by e.g. whole genome sequencing or Next Generation Sequencing, e.g. as described in Qi et al. 2013 (supra) or in Huang et al. 2009 (supra). Especially introgression regions can be easily distinguished from cultivated genomic regions due to the larger amount of genetic variation (SNPs, INDELs, etc.) in the introgression region.

To obtain the introgression fragment present on chromosome 2 and/or 6 from the deposited seeds (NCIMB42262), i.e. to transfer one or both of the introgression fragments comprising the QTLs to another cultivated cucumber plant, a plant is grown from the seed and the plant is crossed with a cultivated cucumber plant to obtain F1 seeds. The F1 hybrid seed and plants grown therefrom, contain one recombinant chromosome 2 and one recombianant 6 from the NCIMB42262 parent and one non-recombinant chromosome 2 and chromosome 6 from the other cultivated parent. To generate new recombination events between the homologous chromosomes, meiosis needs to take place and plants comprising the recombinant chromosomes 2 and/or 6 need to be identified. For example, the F1 can be selfed one or more times to produce F2 or F3 plants (or further selfing generations), and/or F2 plants or F3 plants, etc., can be backcrossed to the cultivated parent. Plants which comprise the QTL2.1 and/or QTL6.1 can be screened for, and selected for, by the presence of one or more of the above SNP markers in order to identify plants comprising a recombinant chromosome 2 and/or 6, comprising the introgression fragment from the deposited seeds, or a smaller introgression fragment (which still comprises the QTL).

Similarly, cultivated cucumber plants comprising QTL2.1 (or a variant thereof) or QTL6.1 (or a variant thereof), can be generated and/or identified using different methods. For example, to obtain a cultivated cucumber plant comprising a introgression fragment from a wild cucumber or wild relative of cucumber, first a wild cucumber or wild relative of cucumber is identified which comprises one or more of the SNP markers associated with QTL2.1 and/or QTLL6.1 disclosed herein, e.g. any one, or more, or all of the markers described herein above. The identified plant is crossed with a cultivated cucumber plant to obtain F1 seeds. The F1 can be selfed to produce F2, F3, etc. plants, and/or F2 plants or F3 plants, etc., can be backcrossed to the cultivated cucumber parent. Plants which are comprising QTL2.1 (or a variant thereof) or QTL6.1 (or a variant thereof) can be screened for, and/or selected for, by the presence of one or more of the above SNP markers and/or screened for, and/or selected for, an increased yield phenotype compared to the initial cultivated parent (lacking the introgressions). Alternatively or in addition, QTL mapping can be carried out in order to identify further molecular markers linked to the QTL2.1 (or a variant thereof) and/or QTL6.1 (or a variant thereof) and/or to generate cultivated cucumber plants comprising an introgression fragment on chromosome 2 and/or 6 which confers significantly enhanced yield.

In one embodiment the presence of the introgression fragment in a cultivated cucumber plant, or the chromosome 2 region (or orthologous chromosome 2 region), comprising QTL2.1, is detectable by a molecular marker assay which detects at least one of the markers selected from the group consisting of:
a) the AG or GG genotype for the Single Nucleotide Polymorphism marker SNP_01 in SEQ ID NO: 1;
b) the AG or AA genotype for the Single Nucleotide Polymorphism marker SNP_11 in SEQ ID NO: 11;
c) any wild cucumber or wild relative of cucumber genome-specific marker in between marker SNP_01 and SNP_11;
d) any wild cucumber or wild-relative of cucumber genome-specific marker which is genetically linked within 7 cM, 5 cM, 3 cM or less of marker SNP_01 or SNP_11; and e) any wild cucumber or wild-relative of cucumber genome-specific marker which is physically linked within 5 Mb, 3 Mb, 2 Mb, 1 Mb, 0.5 Mb or 0.2 Mb or less of marker SNP_01 or SNP_11.

In one aspect the markers of c) are one or more of SNP_02 to SNP_10.

In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected.

Any wild cucumber or wild-relative of cucumber genome-specific marker in between the marker of a) and b) refers to any molecular marker which maps genetically to the chromosome 2 region in-between marker SNP_01 and SNP_11 and/or which lies physically in-between marker SNP_01 and SNP_11, and which is indicative of the wild cucumber chromosome 2 region or of the wild-relative of cucumber chromosome 2 region. This means that the marker is polymorphic between the cultivated cucumber genome and the wild cucumber or wild-relative of cucumber genome. In one aspect, the marker is a Single Nucleotide Polymorphism (SNP), but other molecular markers such as RFLP, AFLP, RAPD, DNA sequencing, etc. may equally be used.

In one embodiment the presence of the introgression fragment in a cultivated cucumber plant, or the chromosome 6 region (or orthologous chromosome 6 region), comprising QTL6.1, is detectable by a molecular marker assay which detects at least one of the markers selected from the group consisting of:
a) the AG or AA genotype for the Single Nucleotide Polymorphism marker SNP_12 in SEQ ID NO: 12;
b) the GT or TT genotype for the Single Nucleotide Polymorphism marker SNP_30 in SEQ ID NO: 30;
c) any wild cucumber or wild relative of cucumber genome-specific marker in between marker SNP_12 and SNP_30;
d) any wild cucumber or wild-relative of cucumber genome-specific marker which is genetically linked within 7 cM, 5 cM, 3 cM or less of marker SNP_12 or SNP_30; and
e) any wild cucumber or wild-relative of cucumber genome-specific marker which is physically linked within 5 Mb, 3 Mb, 2 Mb, 1 Mb, 0.5 Mb or 0.2 Mb or less of marker SNP_12 or SNP_30.

In one aspect the markers of c) are one or more of SNP_13 to SNP_29.

In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected.

Any wild cucumber or wild-relative of cucumber genome-specific marker in between the marker of a) and b) refers to any molecular marker which maps genetically to the chromosome 6 region in-between marker SNP_12 and SNP_30 and/or which lies physically in-between marker SNP_12 and SNP_30, and which is indicative of the wild cucumber chromosome 6 region or of the wild-relative of cucumber chromosome 6 region. This means that the marker is polymorphic between the cultivated cucumber genome and the wild cucumber or wild-relative of cucumber genome. In one aspect, the marker is a Single Nucleotide Polymorphism (SNP), but other molecular markers such as RFLP, AFLP, RAPD, DNA sequencing, etc. may equally be used.

The introgression fragment in the plants of the invention is in one aspect a fragment of the chromosome 2 or 6 which is present in seeds deposited under accession number NCIMB 42262 or a smaller version of that fragment retaining the QTL (generated by e.g. recombination within the introgression fragment).

The introgression fragment is in one aspect equal to or less than 10 Mb in size, preferably equal to or less than 8 Mb, 5 Mb, 3 Mb, 2.5 Mb, 2 Mb, 1.5 Mb, 1 Mb in size. In a further aspect the introgression fragment is at least 0.5 Mb or at least 1 Mb in size.

Also provided are seeds from which a plant of the invention can be grown, as are cucumber fruits harvested from a plant of the invention and comprising the recombinant chromosome 2 and/or 6 in their genome. Likewise a plant cell, tissue or plant part of a plant or of a seed is provided comprising at least one recombinant chromosome 2 and/or 6, wherein said recombinant chromosome 2 and/or 6 comprises an introgression fragment from a wild cucumber plant or wild relative of cucumber and wherein said introgression fragment comprises an allele conferring significantly enhanced fruit yield.

The molecular markers described herein may be detected according to standard method. For example SNP markers can easily be detected using a KASP-assay (see www.kpbioscience.co.uk) or other assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP assay method.

Thus, in one aspect, the SNP markers and the presence/absence of the marker associated with the yield QTL is determined using a KASP assay, but equally other assays can be used. For example, optionally DNA sequencing may also be used.

The physical size of an introgression fragment can be determined by various methods, such as physical mapping, sequencing or by visualization of the introgression using Fluorescent in situ hybridization (FISH) images (Verlaan et al. 2011, Plant Journal 68: 1093-1103).

Plants with smaller introgression fragments on chromosome 2 and/or 6 can be generated by generating new recombinant plants from a population of plants derived from a cross between a cultivated cucumber plant (lacking the introgressions) and a plant of the invention and selecting recombinant progeny having smaller introgression sizes.

In tomato, for example the large *S. chilense* introgression fragment on chromosome 6 (about 27 cM) which comprises the Ty-3 allele has been reduced by selecting a recombinant progeny line (LA1931-AL-F2), which comprises a much smaller *S. chilense* introgression fragment (about 6 cM) comprising Ty-3 (see Ji et al. 2007, Mol. Breeding 20: 271-284).

The cultivated cucumber plant according to the invention may be an inbred an OP (open pollinated variety) or an F1 hybrid. In one aspect the F1 hybrid comprises one or both of the introgression fragments in heterozygous form, i.e. produced by crossing two inbred parent lines, one of which possesses the introgression fragments (preferably in homozygous form, although not necessarily) and collecting the F1 hybrid seeds from said cross. The F1 hybrid may also comprise one or both of the introgression fragment in homozygous form, i.e. produced by crossing two inbred parent lines, each comprising the introgression fragment in homozygous or heterozygous form.

The cultivated cucumber plant may be of any type. Preferably it has good agronomic and good fruit quality characteristics. The cultivated cucumber plant is in one aspect uniform, both genetically and phenotypically. Especially fruit characteristics are uniform, e.g. regarding shape, skin color, skin thickness, skin ribs, skin toughness, spines (spine color, spine density, etc.), presence/absence of warts, length and diameter at edible maturity, flavour, etc. Likewise seed characteristics (i.e. characteristics of the seeds from which the plant is grown) are uniform, e.g. seed size, seed color, etc. Thus, plants of the line or variety comprising the QTL(s) in homozygous or heterozygous form produce uniform fruits, meaning that there is little variation between fruits of plants grown under the same environmental conditions and when fruits are at the same developmental stage (e.g. for qualitative characteristics at least 98%, 99% or preferably 100% of all plants or plant parts, fruits or seed are identical for the characteristics; for quantitative characteristics at least 90%, 95%, 98% of all plants or plant parts, fruits or seed are identical for the characteristics).

The cultivated cucumber plant comprising QTL2.1 and/or QTL6.1 (or variants of either of these) according to the invention may be of any type, e.g. it may be of one of the following cucumber types: pickling cucumbers (e.g. American pickling, European pickling type), slicing cucumbers (e.g. American slicing), long cucumbers, short cucumbers, European greenhouse cucumbers, Beit-Alpha type cucumbers, oriental trellis type cucumbers, Asian cucumbers (e.g. selected from Indian Mottled cucumber, Chinese Long cucumber, Korean cucumber and Japanese cucumber type). In one aspect the cultivated cucumber according to the invention is an inbred line or a F1 hybrid of a pickling cucumber type, slicing cucumber type, long cucumber type, short cucumber type, European greenhouse cucumbers, Beit-Alpha type cucumbers, oriental trellis type cucumbers, Chinese long cucumber type, Korean cucumber type or Japanese cucumber type.

The plant may be a single cross F1 hybrid or an inbred line, comprising one or both QTLs in homozygous or heterozygous form. In one aspect it is an F1 hybrid produced by crossing an (inbred) parent plant comprising QTL2.1 and/or QTL6.1 (or variants of either of these) in homozygous form with an (inbred) parent plant lacking QTL2.1 and QTL6.1 (i.e. lacking introgression fragments comprising said QTLs). Thus in one aspect the F1 hybrid is heterozygous for QTL2.1 and/or QTL6.1.

In another aspect it is an F1 hybrid produced by crossing an (inbred) parent plant comprising QTL2.1 and/or QTL6.1 (or variants of either of these) in homozygous form with an (inbred) parent plant that also comprises QTL2.1 and/or QTL6.1 (or variants of either of these) in homozygous form. Thus, in one aspect the F1 hybrid is homozygous for QTL2.1 (and lacks QTL6.1 or is heterozygous for QTL6.1), or homozygous for QTL6.1 (and lacks QTL2.1 or is homozygous for QTL2.1), or homozygous for both QTL2.1 and QTL6.1.

In one aspect the F1 hybrid is a pickling cucumber type, suitable for once-over mechanical harvest. In one aspect the pickling cucumber is the plant of which seeds were deposited under accession number NCIMB 42262, or progeny thereof, whereby the progeny retain QTL2.1 and/or QTL6.1 (as detectable by the presence of one or more markers as described elsewhere).

The cultivated cucumber plant according to the invention may thus be a cucumber plant suitable for once-over mechanical harvest.

In another aspect the plant according to the invention is not a wild cucumber plant or a landrace.

In yet another aspect the plant according to the invention is a cultivated cucumber of the Eurasian cucumber group, the East Asian cucumber group or the Xishuangbanna cucumber group. In another aspect the plant according to the invention is not a cucumber of the Indian cucumber group.

In one embodiment of the invention the cultivated cucumber plant comprising QTL2.1 (or a variant) and/or QTL6.1 (or a variant) produces seedless fruits without pollination, i.e. is parthenocarpic.

In a further embodiment of the invention the cultivated cucumber plant comprising QTL2.1 (or a variant) and/or QTL6.1 (or a variant) is primarily gynoecious or entirely gynoecious.

In a further embodiment of the invention the cultivated cucumber plant comprising QTL2.1 (or a variant) and/or QTL6.1 (or a variant) is uniform and genetically stable regarding the morphological characteristics of the fruits produced by said plant, e.g. regarding fruit shape, fruit color, skin thickness, warts, etc.

Fruit characteristics, such as average fruit length, average fruit diameter, skin thickness, presence/absence of warts, spininess, skin toughness, skin color, fruit neck shape, fruit tapering, shape of medial cross section, presence or absence of seeds (parthenocarpy), etc. depend on the cucumber type, i.e. the cultivated genetic background (gene pool) into which the QTL(s) is/are introgressed. Thus, depending on the cucumber type, various fruit shapes, sizes and fruit types are included herein. In one aspect the fruits are seedless.

The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as developing and large seeds are not palatable.

In one aspect the plant of the invention is a pickling type (processing type) and produces fruits which at edible maturity have an average fruit length of at least 10 cm, or at least 11 cm, or at least 12 cm, or at least 13 cm and/or a fruit length to diameter ratio of at least 2, at least 2.5, at least 3, or more.

In a different aspect the plant of the invention is a fresh market type, e.g. a long cucumber type or slicing type, and produces fruits have an average fruit length at edible maturity which is longer than the pickling type, e.g. at least 15 cm, 16 cm, 17 cm, 18 cm, 19 cm, 20 cm, 25 cm, 30 cm, 32 cm, 40 cm, or more.

In one aspect the plant is an indeterminate cucumber. In another aspect the cucumber is determinate.

Also seeds from which a plant according to the invention can be grown is provided herein, as are cucumber fruits harvested from a plant according to the invention. These comprise the QTL(s) in their genome and can therefore be distinguished from other fruits by the presence of one or more of the SNP markers provided herein.

In one aspect the fruits are bitter free (selected from the groups bitter and bitterfree) at edible harvest.

In a further aspect the fruit has a thin skin (selected from the groups thick and thin) at edible harvest.

In a different embodiment the QTL(s) are introgressed into a cucumber type called 'Compact', as described in U.S. Pat. No. 8,710,303B2. Thus, the cucumber plants according to the invention comprise the compact gene as described in U.S. Pat. No. 8,710,303B2 in homozygous or heterozygous form, e.g. as present in varieties Hi-Jack and Hi-Lisa (both Nunhems).

A further embodiment of the invention is a plant cell, tissue or plant part of a plant or of a seed according to the invention comprising at least one recombinant chromosome 2 and/or one recombinant chromosome 6, wherein said recombinant chromosome 2 and/or 6 comprises an introgression fragment from a wild cucumber plant or from a wild relative of cucumber and wherein said introgression fragment comprises a QTL conferring enhanced fruit yield.

Also the use of a recombinant chromosome 2 and/or 6 comprising an introgression fragment from a wild cucumber plant or from a wild relative of cucumber (said introgression fragment comprising an allele conferring enhanced fruit yield) for breeding cucumber varieties having enhanced fruit yield is encompassed herein. In one aspect said recombinant chromosomes 2 and/or 6 is the recombinant chromosome 2 and/or 6 as found in seeds deposited under accession number NCIMB 42262, or is derived from said recombinant chromosome 2 and/or 6 (e.g. is a smaller fragment of the introgression fragment found in said seeds).

Likewise, the use of a chromosome 2 and/or 6 as found in seeds deposited under accession number NCIMB 42262, or in progeny thereof, for generating a cultivated cucumber plant comprising an introgression fragment on said chromosome 2 and/or 6 is encompassed herein, wherein said introgression fragment confers enhanced fruit yield compared to the genetic control cucumber plant lacking said introgression fragment(s).

Similarly the use of plants grown from seeds deposited under accession number NCIMB 42262 or progeny thereof, for generating a cultivated cucumber plant comprising enhanced fruit yield is encompassed herein, wherein said enhanced fruit yield is conferred by an introgression fragment obtained from chromosome 2 and/or 6 of said plants or progeny thereof.

Also a method for identifying a cultivated *C. sativus* var. *sativus* plant comprising an introgression fragment on chromosome 2 and/or on chromosome 6 is provided, wherein said introgression fragment is as found in NCIMB 42262, or a smaller fragment derived therefrom, comprising:
a) providing a population of cultivated *C. sativus* var. *sativus* plants,
b) screening said population using a molecular marker assay which detects at least one SNP marker selected from the group consisting of:
i) SNP_01 to SNP_11 for detecting the introgression fragment on chromosome 2 and/or
ii) SNP_12 to SNP_30 for detecting the introgression fragment on chromosome 6;
c) identifying and/or selecting a plant comprising:
iii) at least one of the SNP markers of SNP_01 to SNP_11 for detecting the introgression fragment on chromosome 2 and/or at least one of the SNP markers of SNP_12 to SNP_30 for detecting the introgression fragment on chromosome 6; or
iv) at least 2, 3, or 4 consecutive markers selected from SNP_1 to SNP_11 for detecting the introgression fragment on chromosome 2; and/or at least 2, 3, or 4 consecutive markers selected from SNP_12 to SNP_30 for detecting the introgression fragment on chromosome 6; or
v) at least 1, 2, or 3 markers selected from the group consisting of SNP_2, SNP_5, SNP_7, SNP_9 and SNP10 for detecting the introgression fragment on chromosome 2; and/or at least 1, 2, or 3 markers selected from the group consisting of SNP_12, SNP_13, SNP_18 to SNP_26, SNP_28 and SNP_30 for detecting the introgression fragment on chromosome 6; or
vi) at least marker SNP_06 and optionally also marker SNP_05 and/or SNP_07 for detecting the introgression fragment on chromosome 2; and/or at least 1, 2 or 3 markers selected from SNP_13, SNP_18 and SNP_28 for detecting the introgression fragment on chromosome 6.

Further a method of producing *C. sativus* F1 hybrid plants comprising an introgression fragment conferring enhanced fruit yield is provided comprising:
a) providing a first inbred cucumber plant comprising a recombinant chromosome 2 and/or a recombinant chromosome 6 in homozygous form having an introgression fragment comprising an allele conferring enhanced yield, wherein said introgression fragment is as in NCIMB 42262 or a smaller fragment,
b) providing a second inbred cucumber plant,
c) crossing said cucumber plant of a) with said cucumber plant of b),
d) collecting F1 hybrid seeds from said cross.

In another aspect a method for generating progeny of NCIMB 42262 is provided, said method comprising:
a) growing a plant from seeds deposited under accession number NCIMB 42262;
b) selfing said plant one or more times or crossing said plant one or more times with another cucumber plant to generate progeny seeds;
c) screening said progeny seeds or plants grown from said seeds or parts of the seeds or plants using a molecular marker assay which detects at least one SNP marker selected from the group consisting of:
i) SNP_01 to SNP_11 for detecting the introgression fragment on chromosome 2 and/or
ii) SNP_12 to SNP_30 for detecting the introgression fragment on chromosome 6;
d) identifying and/or selecting a progeny plant comprising:
iii) at least 1 of the SNP markers of SNP_01 to SNP_11 for detecting the introgression fragment on chromosome 2 and/or at least 1 of the SNP markers of SNP_12 to SNP_30 for detecting the introgression fragment on chromosome 6; or
iv) at least 2, 3, or 4 consecutive markers selected from SNP_1 to SNP_11 for detecting the introgression fragment on chromosome 2; and/or at least 2, 3, or 4 consecutive markers selected from SNP_12 to SNP_30 for detecting the introgression fragment on chromosome 6; or
v) at least 1, 2, or 3 markers selected from the group consisting of SNP_2, SNP_5, SNP_7, SNP_9 and SNP_10 for detecting the introgression fragment on chromosome 2; and/or at least 1, 2, or 3 markers selected from the group consisting of SNP_12, SNP_13, SNP_18 to SNP_26, SNP_28 and SNP_30 for detecting the introgression fragment on chromosome 6; or
vi) at least marker SNP_06 and optionally also marker SNP_05 and/or SNP_07 for detecting the introgression fragment on chromosome 2; and/or at least 1, 2 or 3 markers selected from SNP_13, SNP_18 and SNP_28 for detecting the introgression fragment on chromosome 6.

A progeny plant generated by the above method is also an aspect of the invention.

Also containers and packages containing or comprising seeds from which plants of the invention can be grown are provided herein. These may be labelled as containing cultivated cucumber seeds producing enhanced or high fruit yield.

Also progeny seeds and progeny plants of plants of the invention are provided, which retain the introgression on chromosome 2 and/or 6, or a smaller introgression which still confers enhanced yield. Progeny may be any generation obtained by selfing a cucumber plant according to the invention and/or crossing a cucumber plant according to the invention with another cucumber plant one or more times. Progeny are, therefore, either the generation (seeds) produced from the first cross (F1) or selfing (Si), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another cucumber plant (and/or with a wild relative of cucumber). Progeny are preferably selected to retain the recombinant chromosome 2 and/or 6 comprising the introgression fragment from wild cucumber or from a wild relative of cucumber. Thus progeny also have the increased yield phenotype, preferably the same yield as the plant used in the initial cross or selfing. The presence of (or retention of) the introgression fragment comprising the QTL can be determined phenotypically and/or using the molecular marker assay(s) described herein. Regarding phenotypic assessment, of course consideration needs to be given to the dominance nature of the QTLs.

In a further aspect parts of the cucumber plants according to the invention are provided. Parts include for example cells and cell-cultures, tissue cultures, vegetative plant tissues (leaves, roots, etc.), flowers, pollen, embryos, fruits, parts of fruits, etc. The plant parts comprise the introgression fragment on chromosome 2 and/or 6, as described, and as can be detected using one or more of the markers described. Also, when whole plants are regenerated from such cucumber parts, such as cells, cell- or tissue cultures, the regenerated plants comprise the recombinant chromosome 2 and/or 6, and the yield phenotype.

Thus, also provided is a plant cell, tissue or plant part of a plant or of a seed according to the invention comprising at least one recombinant chromosome 2 and/or 6, wherein said recombinant chromosome 2 and/or 6 comprises an introgression fragment from a wild cucumber or wild relative of cucumber plant and wherein said introgression fragment comprises an allele conferring enhanced fruit yield.

Also in vitro cell cultures and in vitro tissue cultures are encompassed herein, of cells or tissues comprising a recombinant chromosome 2 and/or 6 described. Preferably the cells or tissues can be regenerated into a whole cucumber plant, i.e. the cells are regenerable cells and the tissues comprise regenerable cells. Thus, also vegetative propagations of the plants according to the invention are an embodiment herein. Thus, a vegetatively propagated cultivated cucumber plant is provided which comprises a recombinant chromosome 2 and/or 6 as described herein. In a different aspect non-propagating cells comprising QTL2.1 and/or QTL6.1 are encompassed herein, as are tissues comprising such cells.

In a specific aspect a cucumber fruit harvested from a plant according to the invention is provided. Marketable cucumber fruits, especially for the fresh market (slicing), are generally graded according to fruit size and quality characteristics after harvest. See e.g. the United States Standards for Grades of Cucumbers, US Department of Agriculture, Effective Mar. 1, 1985 and reprinted January 1997. Herein different grades of cucumbers are distinguished. Thus, in one aspect harvested fruits are provided of U.S. Fancy grade, U.S. Extra No. 1 grade, U.S. No. 1 grade, U.S. No. 1 Small grade, U.S. No. 1 Large grade, U.S. No. 2 grade. Also containers or packages comprising or consisting of harvested cucumber fruits are provided. Again, the cells of the fruits are distinguishable from other cucumber fruits by the presence of the recombinant chromosome 2 and/or 6 (as determinable in one or more of the molecular marker assays).

In another aspect the cucumber is a pickling type and fruits harvested and optionally pickled are provided.

The invention also provides for a food or feed product comprising or consisting of a plant part described herein preferably a cucumber fruit or part thereof and/or an extract from a plant part described herein. The food or feed product may be fresh or processed, e.g., pickled, canned, steamed, boiled, fried, blanched and/or frozen, etc. For example, containers such as cans, boxes, crates, bags, cartons, Modified Atmosphere Packaging, films (e.g. biodegradable films), etc. comprising plant parts such as fruits or fruit parts (fresh and/or processed) described herein are also provided herein.

Methods and Uses According to the Invention

In a further embodiment, the invention provides for a method of producing a new cultivated cucumber plant which comprises an introgression fragment on chromosome 2 and/or 6 (which confers enhanced yield) in homozygous or heterozygous form, as described. The method comprises crossing a plant of the invention, or a progeny plant thereof, either as male or as female parent, with a second cucumber plant (or a wild relative of cucumber) one or more times, and/or selfing a cucumber plant according to the invention, or a progeny plant thereof, one or more times, and selecting progeny from said crossing and/or selfing.

Thus, a method for transferring the recombinant chromosome 2 and/or 6, comprising the yield QTL, from one (cultivated) cucumber plant into another (cultivated) cucumber plant is provided, especially into cucumber varieties or breeding lines for which the fruit yield should be increased.

The method comprises the steps of:

a) providing a first cultivate cucumber plant comprising a recombinant chromosome 2 and/or 6 having an introgression fragment comprising an allele conferring enhanced fruit yield in homozygous form, b) providing a second cultivated cucumber plant, especially a plant having a wild type (non-recombinant) chromosome 2 and/or chromosome 6, c) crossing said cucumber plant of a) with said cucumber plant of b), d) collecting F1 hybrid seeds from said cross and e) optionally selfing the plant grown from said F1 hybrid seeds to produce F2 seeds or further selfing generations, and optionally selecting the F2 seeds or further selfing generation seeds having the recombinant chromosome 2 and/or 6, and f) optionally breeding further with plants grown from said F1 or F2 or further generation selfing seeds to produce a cucumber plant having good agronomic characteristics and comprising one or both of the introgression fragments in homozygous or heterozygous form.

The presence or absence of the recombinant chromosome 2 and/or 6, and of the introgression fragment, may be determined by one or more of the molecular marker assays described herein and/or by determining whether the yield is significantly increased compared to the plant of b). Further breeding in step f) may comprise selfing, crossing, double haploid production, backcrossing, and combinations thereof (e.g. backcrossing and selfing), etc. Plants and seeds obtainable by the above method are encompassed herein. In one aspect the plant of step a) may be a plant grown from seeds deposited under NCIMB42262, or progeny thereof, or a plant comprising the introgression fragment on chromosome 2 and/or 6 as present in seeds deposited under NCIMB42262, or a shorter fragment of that fragment.

Also provided is a method of producing cultivated cucumber F1 hybrid plants comprising a yield QTL on chromosome 2 and/or 6 comprising:
a) providing a first inbred cucumber plant comprising at least one recombinant chromosome 2 and/or at least one recombinant chromosome 6 comprising an introgression fragment comprising a yield QTL selected from QTL2.1 or a variant thereof and QTL6.1 or a variant thereof,
b) providing a second inbred cucumber plant comprising at least one recombinant chromosome 2 and/or at least one recombinant chromosome 6 comprising an introgression fragment comprising a yield QTL selected from QTL2.1 or a variant thereof and QTL6.1 or a variant thereof,
c) crossing said cucumber plant of a) with said cucumber plant of b),
d) collecting F1 hybrid seeds from said cross.

The inbred cucumber plant of a) and b) may be homozygous and/or heterozygous for the introgression fragment on chromosome 2 and/or 6, and they may contain introgression fragments of different sizes and/or of different origin, i.e. from different wild cucumbers or wild relatives of cucumber. So, for example the introgression fragment in a) may be the same or a different introgression fragment than in b). In one aspect the inbred cucumber plant of a) comprises QTL2.1 or a variant thereof in homozygous form and/or the inbred cucumber plant of b) comprises QTL2.1 or a variant thereof in homozygous form. In one aspect the introgression fragment comprising QTL2.1 is the fragment as found in NCIMB42262 or a smaller fragment thereof. In another aspect the inbred cucumber plant of a) comprises QTL6.1 or a variant thereof in homozygous form and/or the inbred cucumber plant of b) comprises QTL6.1 or a variant thereof in homozygous form. In one aspect the introgression fragment comprising QTL6.1 is the fragment as found in NCIMB42262 or a smaller fragment thereof. In yet another aspect the inbred cucumber plant of a) comprises QTL2.1 or a variant and QTL6.1 or a variant thereof in homozygous form and/or the inbred cucumber plant of b) comprises QTL2.1 or a variant and QTL6.1 or a variant thereof in homozygous form. In one aspect the introgression fragment comprising QTL2.1 and QTL6.1 is the fragment as found in NCIMB42262 or a smaller fragment thereof.

The F1 hybrid seeds preferably comprise at least one recombinant chromosome 2 and/or 6 and the F1 plants grown from the seeds do therefore produce enhanced fruit yield compared to the genetic control.

Plants and seeds obtainable by the above method are encompassed herein.

In a different aspect a method for producing a cultivated cucumber plant comprising an introgression fragment on chromosome 2 and/or 6, wherein said introgression fragment comprises a yield QTL, is provided, said method comprising the steps:
a) providing a first cultivated cucumber plant,
b) providing a second wild cucumber plant or wild relative of cucumber, wherein said plant comprises QTL2.1 (or a variant thereof) and/or QTL6.1 (or a variant thereof) as determinable by the presence of one or more SNP markers as described herein,
c) crossing said cucumber plant of a) with said cucumber plant of b),
d) collecting F1 seeds from said cross and backcrossing an F1 plant to the cucumber plant of a) to produce a backcross (BC1) population, or selfing said F1 plants one or more times to produce an F2 or F3 or higher generation selfing population,
e) optionally backcrossing a plant of d) one or more times to the cucumber plant of a) to produce a higher generation backcross population, and
f) identifying a F2, F3, or higher generation selfing, or BC1 or higher generation backcross plant which comprises an introgression on chromosome 2 and/or 6, wherein said introgression fragment comprises QTL2.1 (or a variant thereof) and/or QTL6.1 (or a variant thereof).

When referring to backcross populations in the method, the backcross populations may also be selfed, i.e. BC1S1, BC1S2, BC2S1, BC2S2, or others.

In one or more of steps b) to f) the presence of the QTL (or the introgression fragment comprising the QTL) may be tested (and plants may be selected) by carrying out a molecular marker assay as described elsewhere herein, e.g. by determining whether the plant comprises the one or more of the SNP markers (e.g. one or more of SNP_01 to SNP_11 and/or one or more of SNP_12 to SNP_30; and/or any wild cucumber or wild-relative of cucumber genome-specific marker in between the marker SNP_01 and SNP_11 or in between SNP_12 and SNP_30).

Using this method, one can generate and/or select new cultivated cucumber plants comprising an introgression with QTL 2.1 (or a variant) and/or QTL 6.1 (or a variant) from a wild source, such as a wild cucumber or wild relative of cucumber.

In one aspect the method for producing a cultivated cucumber plant comprising an introgression fragment on chromosome 2 and/or 6, wherein said introgression fragment comprises a yield QTL, comprises the steps:
a) providing a first cultivated cucumber plant,
b) providing a second wild cucumber plant or wild relative of cucumber comprising one or more of the SNP markers provided herein,
c) crossing said plant of a) with said plant of b),
d) collecting F1 seeds from said cross and backcrossing an F1 plant to the cucumber plant of a) to produce a backcross (BC1) population, or selfing said F1 plants one or more times to produce an F2 or F3 population,
e) optionally selfing the backcross population to produce e.g. a BC1S1 or BC1S2 population,
f) identifying a F2, F3, BC1 BC1S1, or BC1S2 plant which comprises the (one or more) SNP markers and/or any wild cucumber or wild-relative of cucumber genome-specific marker in between the SNP markers.

Also provided is a method for identifying a wild cucumber plant or wild relative of cucumber comprising a yield QTL on chromosome 2 and/or 6, said method comprising:
a) providing a wild cucumber or wild relative of cucumber accession or several accessions;
b) screening said accession(s) using a molecular marker assay which detects at least one (or at least 2, 3, 4, 5, 6, 7, 8, 9, 10 or more) SNP marker selected from the group consisting of: SNP_01 to SNP_11 and/or SNP_12 to SNP_30;
c) identifying and/or selecting an accession from b) comprising at least one or more of the following markers:

a) the AG or GG genotype for the Single Nucleotide Polymorphism marker SNP_01 in SEQ ID NO: 1; and/or
b) the AG or GG genotype for the Single Nucleotide Polymorphism marker SNP_02 in SEQ ID NO: 2; and/or
c) the AG or GG genotype for the Single Nucleotide Polymorphism marker SNP_03 in SEQ ID NO: 3; and/or
d) the GT or GG genotype for the Single Nucleotide Polymorphism marker SNP_04 in SEQ ID NO: 4; and/or
e) the AC or CC genotype for the Single Nucleotide Polymorphism marker SNP_05 in SEQ ID NO: 5; and/or
f) the CT or TT genotype for the Single Nucleotide Polymorphism marker SNP_06 in SEQ ID NO: 6; and/or
g) the AG or GG genotype for the Single Nucleotide Polymorphism marker SNP_07 in SEQ ID NO: 7; and/or
h) the CT or TT genotype for the Single Nucleotide Polymorphism marker SNP_08 in SEQ ID NO: 8; and/or
i) the CT or CC genotype for the Single Nucleotide Polymorphism marker SNP_09 in SEQ ID NO: 9; and/or
j) the GT or GG genotype for the Single Nucleotide Polymorphism marker SNP_10 in SEQ ID NO: 10; and/or
k) the AG or AA genotype for the Single Nucleotide Polymorphism marker SNP_11 in SEQ ID NO: 11; and/or
l) any wild cucumber genome-specific or wild-relative of cucumber genome-specific marker in between marker SNP_01 and SNP_11; and/or
d) identifying and/or selecting an accession from b) comprising at least one or more of the following markers:
a) the AG or AA genotype for the Single Nucleotide Polymorphism marker SNP_12 in SEQ ID NO: 12; and/or
b) the AG or AA genotype for the Single Nucleotide Polymorphism marker SNP_13 in SEQ ID NO: 13; and/or
c) the AG or GG genotype for the Single Nucleotide Polymorphism marker SNP_14 in SEQ ID NO: 14; and/or
d) the CT or TT genotype for the Single Nucleotide Polymorphism marker SNP_15 in SEQ ID NO: 15; and/or
e) the AG or AA genotype for the Single Nucleotide Polymorphism marker SNP_16 in SEQ ID NO: 16; and/or
f) the CT or TT genotype for the Single Nucleotide Polymorphism marker SNP_17 in SEQ ID NO: 17; and/or
g) the CT or CC genotype for the Single Nucleotide Polymorphism marker SNP_18 in SEQ ID NO: 18; and/or
h) the AC or AA genotype for the Single Nucleotide Polymorphism marker SNP_19 in SEQ ID NO: 19; and/or
i) the AC or AA genotype for the Single Nucleotide Polymorphism marker SNP_20 in SEQ ID NO: 20; and/or
j) the AG or GG genotype for the Single Nucleotide Polymorphism marker SNP_21 in SEQ ID NO: 21; and/or
k) the CT or CC genotype for the Single Nucleotide Polymorphism marker SNP_22 in SEQ ID NO: 22; and/or
l) the AG or AA genotype for the Single Nucleotide Polymorphism marker SNP_23 in SEQ ID NO: 23; and/or
m) the CT or CC genotype for the Single Nucleotide Polymorphism marker SNP_24 in SEQ ID NO: 24; and/or
n) the AG or GG genotype for the Single Nucleotide Polymorphism marker SNP_25 in SEQ ID NO: 25; and/or
o) the CT or CC genotype for the Single Nucleotide Polymorphism marker SNP_26 in SEQ ID NO: 26; and/or
p) the AG or AA genotype for the Single Nucleotide Polymorphism marker SNP_27 in SEQ ID NO: 27; and/or
q) the CT or CC genotype for the Single Nucleotide Polymorphism marker SNP_28 in SEQ ID NO: 28; and/or
r) the CT or CC genotype for the Single Nucleotide Polymorphism marker SNP_29 in SEQ ID NO: 29; and/or
s) the GT or TT genotype for the Single Nucleotide Polymorphism marker SNP_30 in SEQ ID NO: 30; and/or
t) any wild cucumber genome-specific or wild-relative of cucumber genome-specific marker in between marker SNP_12 and SNP_30;
and optionally introgressing said QTL from said wild accession into cultivated cucumber (e.g. by backcrossing).

In step b), c) and d) also other molecular marker tests described elsewhere herein can be used. With this method one can, thus, screen wild cucumber accessions or wild relatives of cucumber for the presence of one or more of the markers and, thus, the presence of QTL2.1 and/or QTL6.1 (or variants of these) and introgress the QTLs into cultivated cucumber plants. Plants and seeds obtained by this method are also an embodiment of the invention.

In still another aspect a method for identifying a cultivated cucumber plant comprising an introgression fragment on chromosome 2 and/or 6, wherein said introgression fragment comprises a yield QTL, is provided, said method comprising: screening a cultivated cucumber plant or a population of cultivated cucumber plants or parts of such cucumber plants (e.g. fruits, cells, DNA) using a molecular marker assay which detects at least one SNP marker indicative of QTL2.1 and/or QTL6.1 as described elsewhere herein.

In this method any of the molecular marker tests described elsewhere herein can be used. Thus, using this method one can detect the presence of an introgression fragment on chromosome 2 and/or 6 comprising QTL2.1 and/or QTL6.1 in cultivated cucumber plants or plant parts.

In yet another aspect a method for detecting whether a cultivated cucumber plant comprises an introgression fragment on chromosome 2 and/or 6, wherein said introgression fragment comprises QTL2.1 and/or QTL6.1, is provided, said method comprising:
a) providing cultivated cucumber plant or a plant part,
b) screening said plant or said plant part (or DNA obtained from said plant or plant part) using a molecular marker assay which detects at least one (preferably at least 2, 3, 4, 5 or more) SNP marker selected from the group consisting of:
i) SNP_01 to SNP_11 and/or any wild cucumber or wild-relative of cucumber genome-specific marker in between the marker SNP_01 and SNP_11; and/or
ii) SNP_12 to SNP_30 and/or any wild cucumber or wild-relative of cucumber genome-specific marker in between the marker SNP_12 and SNP_30.

Molecular marker screening obviously involves obtaining plant material and analyzing the genomic DNA of the material for the marker genotype.

In this method also other molecular marker tests described elsewhere herein can be used.

Also encompassed herein is a method for producing a cultivated cucumber plant comprising an introgression fragment on chromosome 2 and/or 6, wherein said introgression fragment comprises QTL2.1 and/or QTL6.1, respectively, comprising:
a) providing a first cultivated cucumber plant lacking an introgression fragment comprising QTL2.1 and QTL6.1,
b) providing a second cultivated cucumber plant selected from plants grown from seeds deposited under accession number NCIMB42262 or progeny thereof;
c) crossing said plant of a) with said plant of b),
d) collecting F1 seeds from said cross and optionally selfing said F1 plants one or more times to produce an F2 or F3 or further selfing population,
e) optionally backcrossing the F1 plant or an F2 or F3 or further selfing plant to the plant of a) to produce a backcross population,
f) optionally selfing the backcross population one or more times,
g) identifying a F1, F2, F3, further selfing or backcross plant which comprises one or more or all of the SNP marker genotype indicative of the introgression fragment on chromosome 2 and/or indicative of the introgression fragment on chromosome 6.

In a further aspect a method of producing F1 hybrid plants is provided comprising:
a) providing a first inbred cucumber plant comprising at least one recombinant chromosome 2 and/or 6 having an introgression fragment comprising QTL2.1 and/or QTL6.1, wherein said introgression fragment is the fragment as found in NCIMB42262, or a shorter fragment of that introgression fragment,
b) providing a second inbred cucumber plant with or without a recombinant chromosome 2 and/or 6,
c) crossing said plant of a) with said plant of b),
d) collecting F1 hybrid seeds from said cross.

In another aspect a method for generating progeny of NCIMB42262 retaining QTL2.1 and/or QTL6.1 is provided, said method comprising:
a) growing a plant from seeds deposited under accession number NCIMB42262;
b) selfing said plant one or more times or crossing said plant one or more times with another cultivated cucumber plant to generate progeny seeds;
c) screening said progeny seeds or plants grown from said seeds or parts of the seeds or plants using a molecular marker assay which detects at least one SNP marker disclosed herein;
d) identifying and/or selecting a progeny plant comprising at least one, two, three or more of the SNP markers indicative of the introgression fragment comprising the QTL2.1 and/or QTL6.1 (as described elsewhere herein); and
e) optionally confirming the enhanced fruit yield of said progeny plants.

In one aspect the yield in e) is preferably at least the same yield as for plants grown from NCIMB42262 when grown under the same conditions.

One can also use the methods and the markers described herein to reduce the size of the introgression fragment comprising the QTL, i.e. to generate and select recombinants having a smaller introgression fragment on chromosome 2 and/or 6, but which retain the yield enhancing part of the introgression fragment.

In one aspect the invention encompasses the use of a recombinant chromosome 2 and/or 6 comprising an introgression fragment from a wild cucumber plant or wild relative of cucumber, said introgression fragment comprising a yield QTL, for breeding cucumber varieties having enhanced fruit yield.

Also provided is the use of a chromosome 2 and/or 6 as found in seeds deposited under accession number NCIMB42262 or progeny thereof for generating cultivated cucumber plant comprising an introgression fragment of said chromosome 2 and/or 6.

Also provided is the use of plants grown from seeds deposited under accession number NCIMB 42262 or progeny thereof, for generating a cultivated cucumber plant comprising enhanced fruit yield, wherein said enhanced fruit yield is conferred by an introgression fragment obtained from chromosome 2 and/or 6 of said plants or progeny.

DNA and Chromosomes According to the Invention

In one aspect a modified (recombinant) cultivated cucumber chromosome 2 and/or 6 is provided herein, which comprises an introgression fragment of a wild cucumber or wild relative of cucumber, as described throughout the specification. In one aspect the recombinant chromosome is isolated from its natural environment. In another aspect it is in a plant cell, especially in a cucumber cell, especially in a cultivated cucumber cell. Also an isolated part of the recombinant chromosome comprising the QTL is provided herein.

In a further aspect a recombinant nucleic acid molecule, especially a recombinant DNA molecule, is provided which comprises a yield-allele according to the invention. In one aspect the yield-allele is detectable by one or more of the molecular marker assays described herein. Also a DNA vector is provided comprising the recombinant DNA. The recombinant DNA molecule or DNA vector may be an isolated nucleic acid molecule. The DNA comprising the yield-allele may be in a microorgansims, such as a bacterium (e.g. *Agrobacterium*).

The use of such a (isolated or extracted) nucleic acid molecule and/or of such a recombinant chromosome or part thereof for generating plant cells and plants comprising a yield-allele is encompassed herein. In one aspect it may be used to generate transgenic plant cells and transgenic plants, e.g. cucumber cells, cucumber plants and parts (e.g. fruits) comprising the yield allele and the plant comprises an enhanced fruit yield phenotype.

Thus, transgenic plant cells, e.g. transgenic cucumber cells, comprising in their genome a recombinant chromosome 2 and/or 6 as described and/or a recombinant nucleic acid molecule comprising a yield-allele are also an embodiment of the invention. In one aspect the DNA molecule comprising the yield-allele is stably integrated into the cucumber genome.

The yield allele may also be cloned and a chimeric gene may be made, e.g. operably linking a plant expressible promoter to the yield allele. Such a chimeric gene may be introduced into a plant cell and the plant cell may be regenerated into a whole plant to produce a transgenic plant. In one aspect the transgenic plant is a cucumber plant, or a melon plant.

Thus, transgenic plants, especially transgenic cultivated cucumber or melon plants, comprising a yield allele and having increased fruit yield are provided herein.

Especially cells or cell cultures comprising a recombinant chromosome 2 and/or 6 according to the invention are an embodiment, independent whether the recombinant chromosome 2 and/or 6 is introduced by transgenic methods or by breeding methods. The cells are e.g. in vitro and are regenerable into plants comprising the recombinant chromosome 2 and/or 6 of the invention.

Also the molecular marker sequences (and isolated nucleic acid molecules comprising the sequence) disclosed herein and molecular markers in between any of the mentioned molecular markers described herein, linked to the yield QTL2.1 and/or QTL 6.1, and their use in detecting and/or generating cucumber plants comprising said QTLs are encompassed herein.

Seed Deposits

A representative sample of seeds of a hybrid *Cucumis sativus* var *sativus* of the pickling type, designated CUXYLD, comprising QTL2.1 and QTL6.1 in heterozygous form, and the genetic control lacking the two QTLs, designated CUXGC, were deposited by Nunhems B.V. on 2 Jul. 2014 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers NCIMB 42262 (CUXYLD) and NCIMB 42261 (CUXGC).

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe how one can obtain plants according to the invention, comprising QTL2.1 and/or QTL6.1. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard breeding methods are described in 'Principles of Plant breeding', Second Edition, Robert W. Allard (ISBN 0-471-02309-4).

EXAMPLES

Example 1

Identification of Yield QTLs

Population Development

A wild cucumber accession obtained from the USA was crossed with a proprietary pickling cucumber breeding line, HMO1125. HMO1125 is an elite line for the pickling cucumber program for once-over mechanical harvest.

A QTL-discovery population has been developed out of the cross between HMO1125 and the wild accession. During population development only female flowering plants have been kept as to facilitate yield measurements.

SNP markers have been used during several generations to optimize for genome coverage and homozygosity. The BC2S2 population was used to construct a genetic map. 245 BC2S2 plants were self-pollinated to generate BC2S3's. The BC2S2 plants were also crossed with an elite line from the breeding program to create test hybrids. The 245 test hybrids were used in yield trials.

Yield Experiments

The aim of the yield experiment was to measure yield for once-over pickling cucumbers. The 245 test hybrids were sown by hand in peat pots. Three seeds were sown per pot, and per test hybrid 80 pots were sown. The sowing of the peat pots was done in the greenhouse. The peat pots were kept during 48 hours at a temperature of at least 24° C. 4 days after sowing the peat pots were planted in the field. Approximately 3 weeks after plantation, the two best growing plants were maintained per peat pot. The final plant density was 10 plants/m$^2$. From each plot fruits of between 110 and 120 plants were harvested. The exact number of plants per plot was recorded. The yield was measured in two different ways. The total number of fruits per plot were counted and divided by the number of plants of that plot. This results in the yield expressed in average number of fruits per plant (FrPP). The second measurement was to take the fruit weight per plot and divide that by the number of plants to obtain the average yield in grams per plant (GrPP). Only fruits with a diameter bigger than 1.5 cm were measured.

In 2010 two field trials were carried out in The Netherlands. Two other field trials were carried out in Brooks, Oreg. (USA). In all 4 trials the 245 test hybrids were planted in a complete randomized design.

The harvest moment was chosen to maximize the total number of fruits with a diameter between 1.5 cm and 5.0 cm. At harvest all fruits were picked of all plants per plot, but only fruits that had a larger diameter than 1.5 cm were counted and weighed. The yield data of the four trials were used for QTL analysis.

Two QTLs were detected. One QTL on chromosome 2, named QTL2.1 and a one QTL on chromosome 6, named QTL6.1.

Table 1 shows the performance of the test hybrids with the introgression comprising QTL 2.1 versus the test hybrids lacking the introgression on chromosome 2. In all measurements the yield increased in plants comprising the QTL2.1 introgression.

Table 2 shows the performance of the test hybrids with the introgression comprising QTL 6.1 compared with test hybrids not having this introgression. In all measurements the yield increased in plants comprising the QTL6.1 introgression.

TABLE 1

Fruit yield of test hybrids comprising the introgression on chromosome 2 (QTL2.1) versus test hybrids lacking the introgression on chromosome 2. Yield data are based on 2 trials in the Netherlands (NL) and 2 trials in the USA (USA). The yield is expressed in average grams per plant (GrPP) and in average fruits per plant (FrPP) (as described above).

|  | GrPP (NL) | GrPP (USA) |
|---|---|---|
| Test hybrids without QTL2.1 introgression | 179 | 378 |
| Test hybrids with QTL2.1 introgression | 223 | 402 |
| Yield increase for plants with QTL2.1 introgression | 124% | 106% |

|  | FrPP (NL) | FrPP (USA) |
|---|---|---|
| Test hybrids without QTL2.1 introgression | 3.0 | 3.5 |
| Test hybrids with QTL2.1 introgression | 3.3 | 3.6 |
| Yield increase for plants with QTL2.1 introgression | 113% | 103% |

TABLE 2

Yield of test hybrids containing the introgression on chromosome 6 (QTL6.1) versus test hybrids lacking the introgression on chromosome 6. Yield data are based on 2 trials in the Netherlands (NL) and 2 trials in the USA (USA). The yield is expressed in average grams per plant (GrPP) and in average fruits per plant (FrPP) (as described above).

|  | GrPP (NL) | GrPP (USA) |
|---|---|---|
| Test hybrids without QTL6.1 introgression | 176 | 377 |
| Test hybrids with QTL6.1 introgression | 230 | 402 |
| Yield increase for plants with QTL6.1 introgression | 131% | 107% |

|  | FrPP (NL) | FrPP (USA) |
|---|---|---|
| Test hybrids without QTL6.1 introgression | 2.9 | 3.5 |
| Test hybrids with QTL6.1 introgression | 3.3 | 3.6 |
| Yield increase for plants with QTL6.1 introgression | 110% | 103% |

Example 2

Based on the results of the QTL-detection trials, one particular BC2S3-line was selected and crossed to another proprietary elite line (VDS826), to create a new testcross, the hybrid CUXYLD. Seeds of CUXYLD were deposited under number NCIMB42262. CUXYLD has an introgression from the wild donor on chromosome 2 (comprising QTL2.1) and on chromosome 6 (comprising QTL6.1), in heterozygous form.

A direct cross between the recurrent parent HMO1125 and the elite line VDS826 was made. This cross was named CUXGC and seeds of CUXGC were deposited under number NCIMB 42261. CUXGC does not have introgressions of the wild donor and is used as comparison (genetic control) to CUXYLD.

Yield trials with CUXYLD and CUXGC were performed in 2012 and in 2013 in the USA. In both years 3 trials were conducted with three different sowing date. Yield was measured in total for 6 trials (2 years*3 trials).

Trial results of 2012 and 2013 are summarized in table 3 and table 4, respectively. In both years the testcross with introgressions on chromosome 2 and chromosome 6 had a significantly higher yield than the genetic control lacking QTL2.1 and QTL6.1 introgressions.

TABLE 3

Yield measurements in 2012 for 3 trials and 2 replicates per trial of genetic control CUXGC and of CUXYLD. Yield is expressed in average fruits per plant (FrPP).

|  | FrPP Trial 1 | FrPP Trial 2 | FrPP Trial 3 | Average of trials | Yield increase of QTL2.1 and QTL6.1 introgressions (% of CUXGC) |
|---|---|---|---|---|---|
| CUXGC | 2.5 | 4.8 | 4.0 | 3.75 |  |
| CUXYLD (QTL2.1 + QTL6.1) | 3.5 | 5.1 | 5.0 | 4.53 | 121% |

TABLE 4

Yield measurements in 2013 for 3 trials and 2 replicates per trial of genetic control CUXGC and of CUXYLD. Yield is expressed in average fruits per plant (FrPP).

|  | FrPP Trial 1 | FrPP Trial 2 | FrPP Trial 3 | Average of trials | Yield increase of QTL2.1 and QTL6.1 introgressions (% of CUXGC) |
|---|---|---|---|---|---|
| CUXGC | 2.3 | 2.4 | 2.8 | 2.5 |  |
| CUXYLD (QTL2.1 + QTL6.1) | 2.45 | 2.85 | 3.15 | 2.8 | 113% |

Example 3

Single Nucleotide Polymorphism markers (SNPs) were identified spanning the wild introgressions fragment and their position on the physical *C. sativus* map was determined.

TABLE 5

SNP markers for QTL2.1 introgression fragment

| SNP marker | Physical position of SNP (base number) | Genotype of introgression fragment (homoxygous) | Genotype of recurrent parent lacking introgression (HMO1125) | Genotype of hybrid (heterozygous for QTL2.1) | Genomic sequence comprising SNP |
|---|---|---|---|---|---|
| SNP_01 | 433,086 | GG | AA | AG | SEQ ID NO: 1 AAATTTATTAAAGTCTT TTTTTCTCTCTCGATCAT ATATTATTTATATATTT |

TABLE 5-continued

SNP markers for QTL2.1 introgression fragment

| SNP marker | Physical position of SNP (base number) | Genotype of introgression fragment (homoxygous) | Genotype of recurrent parent lacking introgression (HMO1125) | Genotype of hybrid (hetero-zygous for QTL2.1) | Genomic sequence comprising SNP |
|---|---|---|---|---|---|
| | | | | | GTTATCTTTTAACCCTTT GAAC[A/G]ATATAGTTC TTAATTAAAAGTATAGG AGTTGCAACAAAAGAT GGAACAGCCATACCAT ATCCAAAACCAATCCAC |
| SNP_02 | 581,359 | GG | AA | AG | SEQ ID NO: 2 TAAAAGGTTTAAATGTG ATCATAAAGAATTCCAT CTATCTATATTTCATTT ATTAATGTTGTCAACAG TAATAA[A/G]AAGCATT TAACTCTATGTAAAAG ATGAAACAAACAAAAA GTAACTCATAACTTCAA TAGATTTCTTACCATCT M |
| SNP_03 | 1,060,773 | GG | AA | AG | SEQ ID NO: 3 CAAAAAAAAACAAAAA TCAAAAAAAGGAAATT ACATAAAACCTAAAGC CCTAAACCCTAATTCGC TAAAAAAGA[A/G]ACCT AATTTTACGGAAAAGA AAAGAACTAACCTAGA GATGACGTGGCATYAG ATTTTCTCTGGGTCCCA TTTTAA |
| SNP_04 | 1,905,434 | GG | TT | GT | SEQ ID NO: 4 TATTGTTTTGTGGACG TATGATTATCTTAAAAA TTACTTCTAATATATAT TTGGTGAAGCAAGTTTT TCTAAG[G/T]TTAAAAT AAACAATACCTCCAAA CAACTTAGAAAAATGA CTTTTATTGATGTAATS AAAAAAATAAAATGAT CTC |
| SNP_05 | 2,003,490 | CC | AA | AC | SEQ ID NO: 5 TCATASAATGATGATAA CTTTGTGAGCAATGTAA CACAAAGTTAGGTTTAA ACTTACTTTTTTTCATCT AAATT[A/C]TGTCATTTG GTCATATGGATACGTTT GTTTAAAAACAATAATA ATAAAGTAGRTTAGTGT TAAKGCTATATAGAT |
| SNP_06 | 2,089,529 | TT | CC | CT | SEQ ID NO: 6 KCAAATGTTTTCTCTTC TAATTTTTTTTAACATA ATAAAAGATAGAGTAC AAATAGAAATAGTAAA TCGAAAAA[C/T]AAAAA CTAAATATTACGAATTT TGATAAAACTGAAGGA ACAACGAAATAGAAAA AGCAAGGATGTTGCTGC AAAT |
| SNP_07 | 2,181,271 | GG | AA | AG | SEQ ID NO: 7 CATGTCAATCTCAAAGT CTATTCACAAAAAATAC ACCATTTGAGGGAAGA GGGATAATTACAAGGA AAAGAAAA[A/G]CAGTG |

TABLE 5-continued

SNP markers for QTL2.1 introgression fragment

| SNP marker | Physical position of SNP (base number) | Genotype of introgression fragment (homoxygous) | Genotype of recurrent parent lacking introgression (HMO1125) | Genotype of hybrid (hetero-zygous for QTL2.1) | Genomic sequence comprising SNP |
|---|---|---|---|---|---|
| | | | | | ACTAAGTGAAAACAAA TACAAGATTTCATTTTC CACTTATGACTTCAATT TCAAAGATCTTTCGRTC TAT |
| SNP_08 | 2,377,687 | TT | CC | CT | SEQ ID NO: 8 RCATCAACMAAAAAAA AMMAAAAAGGATCCAT CTTGTTCAACACGATTG CCACTTTTCCCTTTGGT CCATTTGG[C/T]TGGAG AGAAACAATCAAATAT TCAGCAACAAAGCCTG AACATAGACTGAATTAT GGGAAGACATTAAATC TCTCA |
| SNP_09 | 2,575,216 | CC | TT | CT | SEQ ID NO: 9 TGGTGCTTCCTTTTCCTC ACTTTTTTTTTAAATTAT GAAATCTCTTAACAGAG TATTCAAGGAAAAGAA GTGTG[C/T]TATAAAAT AAAACTCTCTAAGACTA AAGATATCTATTTGATA ACTACTTTTTTCTTTTG TCATAGACATAGCTA |
| SNP_10 | 2,712,864 | GG | TT | GT | SEQ ID NO: 10 CTGTAAAAATATATACC TAGTTCCTAGATTCCAA CCAGACAAGTTAGCAG CAGTAGTTAAAGCTTCC CTCCAAA[G/T]TTGGGT CTTTGTTTGGAACTTAG GCTGATGTTTGGCCAGT GCTTCTCCGAAGCTACC AGTTTGTTTTCGTATAT C |
| SNP_11 | 2,958,658 | AA | GG | AG | SEQ ID NO: 11 TCGGGATAAKTTTGATT TTGAAAATCCATTTGTT AGAAATTAGAAAGGGT GCATCTCAATTTACACA AAGCTTA[A/G]ACATTC TAGTTGGGATGTTCTTT TTGTCAACCGGAAAGG AGAAAAACATCTAACA AAAATCGAAYGATTAC ATTC |

TABLE 6

SNP markers for QTL6.1 introgression fragment

| SNP marker | Physical position of SNP (base number) | Genotype of introgression fragment (homoxygous) | Genotype of recurrent parent lacking introgression (HMO1125) | Genotype of hybrid (hetero-zygous for QTL6.1) | Genomic sequence comprising SNP |
|---|---|---|---|---|---|
| SNP_12 | 26,833,907 | AA | GG | AG | SEQ ID NO: 12 AATGCAGTATGAACC AGMGGGAGATGAGC TTTCCTGATAATGAT CTTTTGTTTTGATTCC AATGGACCAAAAAA |

TABLE 6-continued

SNP markers for QTL6.1 introgression fragment

| SNP marker | Physical position of SNP (base number) | Genotype of introgression fragment (homoxygous) | Genotype of recurrent parent lacking introgression (HMO1125) | Genotype of hybrid (hetero-zygous for QTL6.1) | Genomic sequence comprising SNP |
|---|---|---|---|---|---|
| | | | | | [A/G]CATATGGAGAAT GAAAACTAAACAAA CCAAATAAGAAGGC ATCTAGACTAGTGTT TGCCATGTACTCATA GACAA |
| SNP_13 | 26,898,765 | AA | GG | AG | SEQ ID NO: 13 AACATAATTATACCT TTTAATCGCTACCAC CTGTTACCAACAATT ATAAGCTTGATGTAG GGTTGGAATAATGT [A/G]ATCAAATTCCAA ACATAATAGTACATA AAAACAAAACTATTT TATTTATTTGTTTGTT ATTYARGTCAAGATC TT |
| SNP_14 | 26,996,095 | GG | AA | AG | SEQ ID NO: 14 ATCWTGCACTAAAG CAAATTAAGACTGTT TTTGCAAAGTTAAAC AAGCTTGAGAAACTT CTTGTAGAGTCCCTG [A/G]GTAAAGATTTGA GCTGTGAGTTACGGA ATTAAGCCAGACAGA CAACCCATTGTCAAC ACCATTTTGGTTTAA TCT |
| SNP_15 | 27,028,370 | TT | CC | CT | SEQ ID NO: 15 TCTTCTCTAACCAAT GTTAGASWTTGTTTG TGTCTAACATATGTA TCATGTACACAGCGG CTGGCTTGCGAAAC [C/T]GGTCTCCTGAAA ACAAAGCAGTCATTG TAAGTGAAGTTGAGA AGATAGTTTGGCCAG CCATTGCAGCAGGCR AGG |
| SNP_16 | 27,357,947 | AA | GG | AG | SEQ ID NO: 16 AATTAAACCCATAAT TTGATAAAGAAATAA AATTAAAAGAAGAA AGAGTGTGACGTGGC TTTCCCAAATCGAAT [A/G]ATGGGATTCCAT CTGGAAGCTTCCACA GTGTTCTGGATCTCT GTTGTTCTTCCAGAC TCATCCTTCTGAACC CCT |
| SNP_17 | 27,388,149 | TT | CC | CT | SEQ ID NO: 17 AATGGAATTATGGTT GGAYTTTTGTTAATA GGTATGAAAACAAAT TTTTATGTTTCCATTA AAGGGACGTCCT[C/T] CTATAATATATGCA AATTAATTAAGGGTA TTAAGGGTGAGAAA AAATTATATATTAAT TGTTGGACATTTGTA TT |

TABLE 6-continued

SNP markers for QTL6.1 introgression fragment

| SNP marker | Physical position of SNP (base number) | Genotype of introgression fragment (homoxygous) | Genotype of recurrent parent lacking introgression (HMO1125) | Genotype of hybrid (hetero-zygous for QTL6.1) | Genomic sequence comprising SNP |
|---|---|---|---|---|---|
| SNP_18 | 27,498,689 | CC | TT | CT | SEQ ID NO: 18 ATAATAGAAGAGGA GGGCATGAGTGGAA GAAACAAGTTCATCT GCTGAAGAAGTTTTG ATATTGAGTTCATAA T[C/T]CTGAAGAGAT TGCAGATTCATGGTG TAAAATGCTAACGAG ATTTAAGTCTTATTA GGAGATTGTAAAAG AAAAAC |
| SNP_19 | 27,581,485 | AA | CC | AC | SEQ ID NO: 19 RTATGTATAGGATTG CAGGATGAYTCTTTA TAGGAGTAATAGTGG GAGGATCAACACTAA TTTTATTGTTTCAC [A/C]ACCTCTGCTTTTAG AAGGAAAGCAATTC ATAGATTTAAATAAT CTCCCAGTCGGAAAA TTCATCATTTTGAAT GG |
| SNP_20 | 27,607,305 | AA | CC | AC | SEQ ID NO: 20 AGGTGAACTTGTGAC ATAGATAAAAAGAA TTATTATTTTAGGGTT TAGAAAGACACAACT TTACTGCTACTATA [A/C]GTGTGAGTTCCAT AAATGAGAGACAAC ATTAGAGGACACCAA CCCAATTTAAACCTA AATTAAAAGGGTTAG AGC |
| SNP_21 | 27,750,242 | GG | AA | AG | SEQ ID NO: 21 TTCCTCAACGATTTG TAGCCTTTGTGACGG TTGGGAGTGCTGATA CGGGCCAACTTGGAA AAGATCTTGAGAAG [A/G]CGGCGGTGGCA GGTGTAGAGAGAGC GGTTAATGGTGGCAA CGACAGCGGAGGGG GCATTCTTGATTGGA GACTTG |
| SNP_22 | 27,840,804 | CC | TT | CT | SEQ ID NO: 22 TTTGGCAAAACTCAG AGAATCAAGAAGGA TTTGGGCAGCTTTTT GTGGTATCGGAGGAG CAGAAGCTTGATTGG [C/T]CAGACATGTTCT ACATAACCACTCTCC CTCTTAATCTAAGGA AGCCTCATCTTTTTC AAAGGCTTCCACCAA AAC |
| SNP_23 | 27,994,675 | AA | GG | AG | SEQ ID NO: 23 GAAAATAKAATTTTC TTCCCAAAGACTCAA AATCCACCCATCTCC AGCCGTCATCTCTCA CGAATTTCGCACGG [A/G]CCCTACAAAATA |

TABLE 6-continued

SNP markers for QTL6.1 introgression fragment

| SNP marker | Physical position of SNP (base number) | Genotype of introgression fragment (homoxygous) | Genotype of recurrent parent lacking introgression (HMO1125) | Genotype of hybrid (heterozygous for QTL6.1) | Genomic sequence comprising SNP |
|---|---|---|---|---|---|
| | | | | | CAATTCTTCTCCAAC ATTATACCGCCACTC TCTTTTTTTATTTCTT TATTATTTCAATATA TA |
| SNP_24 | 28,032,027 | CC | TT | CT | SEQ ID NO: 24 TGTAAAATTTAATGG CAAAAAACTTATGAA ACAAAACAAGTTATT ATAATATTTAATGAA GATTTTTCTTCTTT [C/T]GCTTTATTATAATA TTTGGAGATGTTGAA GACAAAATGCATAA AATTCTAAATATTGG ATGGAAACGTTGGAG CA |
| SNP_25 | 28,291,605 | GG | AA | AG | SEQ ID NO: 25 AATGAGAGCTATCAT AATTATTGCAATAAT ATTGTTCTTTTTATTT GGGGCTCTTTTAATT TTTTTTATGTATT[A/G] GTATTTAAGTAAAA TCATTTGAGTTAAAT CACTAACAAAGAATT GAGAAATTCAATAAT GACCAAAGGGAACT GA |
| SNP_26 | 28,422,518 | CC | TT | CT | SEQ ID NO: 26 CCTCTGTTTCAGCTTC CACAACTTGTATGAT CTTGCACCCTTCAAG CTCTTCGATACCAGG TGTGTGTTTTTTC[C/T] ACTATAACCTAAAC CCTCGCAATGTTTCA AGAAAGGGTATGTGT GTTTTTGTGATTTTAT TCAGATTGAACTCTC |
| SNP_27 | 28,486,699 | AA | GG | AG | SEQ ID NO: 27 GGGATTCATCATYAT GTAMGAAGAGTATC AACTTGTAGGGATAT TTCTTTATAACCCAG ATCAATTTCAGTTTT [A/G]ATAGACGTGATC ACACGTGAGTATAGC ATGCTCTATTTATGC ATAATGCTAAGCGAG TGGTTTTATCTMYGA GGA |
| SNP_28 | 28,545,858 | CC | TT | CT | SEQ ID NO: 28 ACACAATTTATCTCT TCTTCAYCACTGGGG GACCCGGCAACACTT CTCTTTCTTGTCGTCT TCACGTTCTTTAA[C/T] TAATTTCACTTCTG CCCTGCTTCAATAGT AAGTGTTTTGTCTGT TTTTCTGCTGTTTTCA ITTITTCCTTTTTTG |
| SNP_29 | 28,579,652 | CC | TT | CT | SEQ ID NO: 29 CATAAATTATAAGCA TCCAATTACATAAAA |

TABLE 6-continued

SNP markers for QTL6.1 introgression fragment

| SNP marker | Physical position of SNP (base number) | Genotype of introgression fragment (homoxygous) | Genotype of recurrent parent lacking introgression (HMO1125) | Genotype of hybrid (hetero-zygous for QTL6.1) | Genomic sequence comprising SNP |
|---|---|---|---|---|---|
| | | | | | TAAAGTCCCTACCAA CTTTGTTATGTGGTC AAAACAGTCATCTT [C/T]TATGTATATATA ACTCATTAATATATA TAAGTTTATATTCCT AAATTGGATTTGTGT GGATATTATAAAAGT TYA |
| SNP_30 | 28,799,844 | TT | GG | GT | SEQ ID NO: 30 GATTTGATTTTCTTG GTGCTTGTTGATCTG TTCTGCTAATTAAGC ATATTTTTATGAAAT TTATACCGTCTGAA [G/T]TTAAATTTTAAT GTGGATGAGTTACTA ATATTATTGGAAGCT TGCAGATGTTGTGAG GGATGATCCTACGAA CAA |

The invention claimed is:

1. A *Cucumis sativus* var. *sativus* plant, or part thereof, comprising an introgression fragment on chromosome 6 in homozygous or heterozygous form, wherein said introgression fragment is the fragment as found on chromosome 6 in seeds of which a representative sample has been deposited under accession number NCIB 42262, or a smaller fragment derived therefrom, and confers an increase in cucumber fruit yield, and wherein said introgression fragment or smaller fragment comprises at least 1 of the following markers:

a) the AG or AA genotype for the Single Nucleotide Polymorphism marker SNP 12 in SEQ ID NO: 12;

b) the AG or AA genotype for the Single Nucleotide Polymorphism marker SNP 13 in SEQ ID NO: 13;

c) the AG or GG genotype for the Single Nucleotide Polymorphism marker SNP 14 in SEQ ID NO: 14;

d) the CT or TT genotype for the Single Nucleotide Polymorphism marker SNP 15 in SEQ ID NO: 15;

e) the AG or AA genotype for the Single Nucleotide Polymorphism marker SNP 16 in SEQ ID NO: 16;

f) the CT or TT genotype for the Single Nucleotide Polymorphism marker SNP 17 in SEQ ID NO: 17;

g) the CT or CC genotype for the Single Nucleotide Polymorphism marker SNP 18 in SEQ ID NO: 18;

h) the AC or AA genotype for the Single Nucleotide Polymorphism marker SNP 19 in SEQ ID NO: 19;
i) the AC or AA genotype for the Single Nucleotide Polymorphism marker SNP 20 in SEQ ID NO: 20;
j) the AG or GG genotype for the Single Nucleotide Polymorphism marker SNP 21 in SEQ ID NO: 21;
k) the CT or CC genotype for the Single Nucleotide Polymorphism marker SNP 22 in SEQ ID NO: 22;
l) the AG or AA genotype for the Single Nucleotide Polymorphism marker SNP 23 in SEQ ID NO: 23;
m) the CT or CC genotype for the Single Nucleotide Polymorphism marker SNP 24 in SEQ ID NO: 24;
n) the AG or GG genotype for the Single Nucleotide Polymorphism marker SNP 25 in SEQ ID NO: 25;
o) the CT or CC genotype for the Single Nucleotide Polymorphism marker SNP 26 in SEQ ID NO: 26;
p) the AG or AA genotype for the Single Nucleotide Polymorphism marker SNP 27 in SEQ ID NO: 27;
q) the CT or CC genotype for the Single Nucleotide Polymorphism marker SNP 28 in SEQ ID NO: 28;
r) the CT or CC genotype for the Single Nucleotide Polymorphism marker SNP 29 in SEQ ID NO: 29; or
s) the GT or TT genotype for the Single Nucleotide Polymorphism marker SNP 30 in SEQ ID NO: 30.

2. The plant according to claim 1, wherein said increase in cucumber fruit yield is phenotypically expressed as a significantly higher average number of fruits per plant (FrPP) of the plant line comprising the introgression fragment compared to the genetic control line lacking the introgression fragment when grown under the same environment and/or a significantly higher average fruit weight per plant (GrPP) of the plant line comprising the introgression fragment compared to a genetic control line lacking the introgression fragment when grown under the same environment.

3. The plant according to claim 1, wherein said introgression fragment on chromosome 6 comprises at least two of the following markers:
a) the AG or AA genotype for the Single Nucleotide Polymorphism marker SNP_12 in SEQ ID NO: 12;
b) the AG or AA genotype for the Single Nucleotide Polymorphism marker SNP_13 in SEQ ID NO: 13;
c) the AG or GG genotype for the Single Nucleotide Polymorphism marker SNP_14 in SEQ ID NO: 14;
d) the CT or TT genotype for the Single Nucleotide Polymorphism marker SNP_15 in SEQ ID NO: 15;
e) the AG or AA genotype for the Single Nucleotide Polymorphism marker SNP_16 in SEQ ID NO: 16;
f) the CT or TT genotype for the Single Nucleotide Polymorphism marker SNP_17 in SEQ ID NO: 17;
g) the CT or CC genotype for the Single Nucleotide Polymorphism marker SNP_18 in SEQ ID NO: 18;
h) the AC or AA genotype for the Single Nucleotide Polymorphism marker SNP_19 in SEQ ID NO: 19;
i) the AC or AA genotype for the Single Nucleotide Polymorphism marker SNP_20 in SEQ ID NO: 20;
j) the AG or GG genotype for the Single Nucleotide Polymorphism marker SNP_21 in SEQ ID NO: 21;
k) the CT or CC genotype for the Single Nucleotide Polymorphism marker SNP_22 in SEQ ID NO: 22;
l) the AG or AA genotype for the Single Nucleotide Polymorphism marker SNP_23 in SEQ ID NO: 23;
m) the CT or CC genotype for the Single Nucleotide Polymorphism marker SNP_24 in SEQ ID NO: 24;
n) the AG or GG genotype for the Single Nucleotide Polymorphism marker SNP_25 in SEQ ID NO: 25;
o) the CT or CC genotype for the Single Nucleotide Polymorphism marker SNP_26 in SEQ ID NO: 26;
p) the AG or AA genotype for the Single Nucleotide Polymorphism marker SNP_27 in SEQ ID NO: 27;
q) the CT or CC genotype for the Single Nucleotide Polymorphism marker SNP_28 in SEQ ID NO: 28;
r) the CT or CC genotype for the Single Nucleotide Polymorphism marker SNP_29 in SEQ ID NO: 29; and/or
s) the GT or TT genotype for the Single Nucleotide Polymorphism marker SNP_30 in SEQ ID NO: 30.

4. The plant according to claim 1, wherein said introgression fragment on chromosome 6 comprises at least 2 consecutive markers from the following markers:
a) the AG or AA genotype for the Single Nucleotide Polymorphism marker SNP_12 in SEQ ID NO: 12;
b) the AG or AA genotype for the Single Nucleotide Polymorphism marker SNP_13 in SEQ ID NO: 13;
c) the AG or GG genotype for the Single Nucleotide Polymorphism marker SNP_14 in SEQ ID NO: 14;
d) the CT or TT genotype for the Single Nucleotide Polymorphism marker SNP_15 in SEQ ID NO: 15;
e) the AG or AA genotype for the Single Nucleotide Polymorphism marker SNP_16 in SEQ ID NO: 16;
f) the CT or TT genotype for the Single Nucleotide Polymorphism marker SNP_17 in SEQ ID NO: 17;
g) the CT or CC genotype for the Single Nucleotide Polymorphism marker SNP_18 in SEQ ID NO: 18;
h) the AC or AA genotype for the Single Nucleotide Polymorphism marker SNP_19 in SEQ ID NO: 19;
i) the AC or AA genotype for the Single Nucleotide Polymorphism marker SNP_20 in SEQ ID NO: 20;
j) the AG or GG genotype for the Single Nucleotide Polymorphism marker SNP_21 in SEQ ID NO: 21;
k) the CT or CC genotype for the Single Nucleotide Polymorphism marker SNP_22 in SEQ ID NO: 22;
l) the AG or AA genotype for the Single Nucleotide Polymorphism marker SNP_23 in SEQ ID NO: 23;
m) the CT or CC genotype for the Single Nucleotide Polymorphism marker SNP_24 in SEQ ID NO: 24;
n) the AG or GG genotype for the Single Nucleotide Polymorphism marker SNP_25 in SEQ ID NO: 25;
o) the CT or CC genotype for the Single Nucleotide Polymorphism marker SNP_26 in SEQ ID NO: 26;
p) the AG or AA genotype for the Single Nucleotide Polymorphism marker SNP_27 in SEQ ID NO: 27;
q) the CT or CC genotype for the Single Nucleotide Polymorphism marker SNP_28 in SEQ ID NO: 28;
r) the CT or CC genotype for the Single Nucleotide Polymorphism marker SNP_29 in SEQ ID NO: 29; and
s) the GT or TT genotype for the Single Nucleotide Polymorphism marker SNP_30 in SEQ ID NO: 30.

5. The plant according to claim 1, wherein the introgression fragment on chromosome 6 comprises at least 1 of the following markers:
the AG or AA genotype for the Single Nucleotide Polymorphism marker SNP_12 in SEQ ID NO: 12;
the AG or AA genotype for the Single Nucleotide Polymorphism marker SNP_13 in SEQ ID NO: 13;
the CT or CC genotype for the Single Nucleotide Polymorphism marker SNP_18 in SEQ ID NO: 18;
the AC or AA genotype for the Single Nucleotide Polymorphism marker SNP_19 in SEQ ID NO: 19;
the AC or AA genotype for the Single Nucleotide Polymorphism marker SNP_20 in SEQ ID NO: 20;
the AG or GG genotype for the Single Nucleotide Polymorphism marker SNP_21 in SEQ ID NO: 21;

the CT or CC genotype for the Single Nucleotide Polymorphism marker SNP_22 in SEQ ID NO: 22;
the AG or AA genotype for the Single Nucleotide Polymorphism marker SNP_23 in SEQ ID NO: 23;
the CT or CC genotype for the Single Nucleotide Polymorphism marker SNP_24 in SEQ ID NO: 24;
the AG or GG genotype for the Single Nucleotide Polymorphism marker SNP_25 in SEQ ID NO: 25;
the CT or CC genotype for the Single Nucleotide Polymorphism marker SNP_26 in SEQ ID NO: 26;
the CT or CC genotype for the Single Nucleotide Polymorphism marker SNP_28 in SEQ ID NO: 28; and/or
the GT or TT genotype for the Single Nucleotide Polymorphism marker SNP_30 in SEQ ID NO: 30.

6. The plant according to claim 1, wherein the introgression fragment on chromosome 6 comprises at least 1 of the following markers:
the AG or AA genotype for the Single Nucleotide Polymorphism marker SNP_13 in SEQ ID NO: 13;
the CT or CC genotype for the Single Nucleotide Polymorphism marker SNP_18 in SEQ ID NO: 18; and/or
the CT or CC genotype for the Single Nucleotide Polymorphism marker SNP_28 in SEQ ID NO: 28.

7. The plant according to claim 1, wherein the plant is of one of the following cucumber types: pickling cucumbers, slicing cucumbers, long cucumbers, short cucumbers, European greenhouse cucumbers, Beit-Alpha type cucumbers, oriental trellis type cucumbers, or Asian cucumbers.

8. The plant according to claim 1, wherein the plant is a single cross F1 hybrid or an inbred line.

9. The plant according to claim 1, wherein the plant is a suitable for once-over mechanical harvest.

10. The plant according to claim 1, wherein the plant is not a wild cucumber plant or a landrace, or wherein the plant is a cultivated cucumber of the Eurasian cucumber group, the East Asian cucumber group or the Xishuangbanna cucumber group.

11. The plant according to claim 1, wherein the plant produces seedless fruits without pollination.

12. The plant according to claim 1, wherein the plant is primarily or entirely gynoecious.

13. The plant according to claim 1, wherein the plant is uniform regarding the morphological characteristics of the fruits produced by said plant.

14. The plant according to claim 1, wherein the plant produces fruits which at edible maturity have an average fruit length of at least 10 cm and/or a fruit length to diameter ratio of 2 or more.

15. The plant according to claim 1, wherein said introgression fragment on chromosome 6 is the fragment as found on chromosome 6 in seeds deposited under accession number NCIMB42262.

16. The plant according to claim 1, wherein said introgression fragment on chromosome 6 is equal to or less than 10 Mb in size, equal to or less than 8 Mb in size, or equal to or less than 3 Mb in size.

17. The plant according to claim 16, wherein said introgression fragment is at least 0.5 Mb or at least 1 Mb in size.

18. The plant according to claim 1, wherein the plant is an indeterminate cucumber.

19. Seeds from which a plant according to claim 1 can be grown.

20. A cucumber fruit harvested from a plant according to claim 1.

21. The fruit according to claim 20, wherein the fruit is bitter free at edible harvest.

22. The fruit according to claim 20, wherein the fruit has a thin skin at edible harvest.

23. A plant cell, tissue or plant part of the plant according to claim 1.

24. A method for identifying a cultivated C. sativus var. sativus plant comprising an introgression fragment on chromosome 6, wherein said introgression fragment is as found in NCIMB 42262, or a smaller fragment derived therefrom, comprising:
a) screening a population of cultivated C. sativus var. sativus plants using a molecular marker assay which detects at least one SNP marker of: SNP_12 to SNP_30 for detecting the introgression fragment on chromosome 6; and
b) identifying and/or selecting a plant comprising:
i) at least 1 of the SNP markers of SNP_12 to SNP_30 for detecting the introgression fragment on chromosome 6; or
ii) at least 2 consecutive markers from SNP_12 to SNP_30 for detecting the introgression fragment on chromosome 6; or
iii) at least 1 marker from SNP_12, SNP_13, SNP_18 to SNP_26, SNP_28 and/or SNP_30 for detecting the introgression fragment on chromosome 6; or
iv) at least 1, 2 or 3 markers selected from SNP_13, SNP_18 and SNP_28 for detecting the introgression fragment on chromosome 6.

25. A method of producing C. sativus F1 hybrid plants comprising an introgression fragment conferring enhanced fruit yield comprising:
a) crossing a first inbred cucumber plant comprising a recombinant chromosome 6 in homozygous form having an introgression fragment comprising an allele conferring enhanced yield, wherein said introgression fragment is as in NCIMB 42262 with a second inbred cucumber plant, and
b) collecting F1 hybrid seeds from said cross.

26. A method for generating progeny of NCIMB 42262, said method comprising:
a) selfing a plant grown from seeds deposited under accession number NCIMB 42262 one or more times or crossing said plant one or more times with another cucumber plant to generate progeny seeds;
b) screening said progeny seeds or plants grown from said progeny seeds or parts of the progeny seeds or plants using a molecular marker assay which detects at least one of: SNP_12 to SNP_30 for detecting the introgression fragment on chromosome 6, and
c) identifying and/or selecting a progeny plant comprising:
i) at least 1 of the SNP markers of SNP_12 to SNP_30 for detecting the introgression fragment on chromosome 6; or
ii) at least 2 consecutive markers selected from SNP_12 to SNP_30 for detecting the introgression fragment on chromosome 6; or
iii) at least 1 marker from SNP_12, SNP_13, SNP_18 to SNP_26, SNP_28 and SNP_30 for detecting the introgression fragment on chromosome 6; or
iv) at least 1 marker selected from SNP_13, SNP_18 and SNP_28 for detecting the introgression fragment on chromosome 6.

27. A progeny plant generated by the method of claim 26, wherein said progeny plant comprises an introgression fragment on chromosome 6 in homozygous or heterozygous form, wherein said introgression fragment is the fragment as found on chromosome 6 in seeds of which a representative sample has been deposited under accession number NCIMB 42262, or a smaller fragment derived therefrom.

\* \* \* \* \*